(12) United States Patent
Bikovsky

(10) Patent No.: US 8,187,228 B2
(45) Date of Patent: *May 29, 2012

(54) INFUSION PUMPS AND METHODS AND DELIVERY DEVICES AND METHODS WITH SAME

(75) Inventor: Rafi Bikovsky, Oak Park, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 610 days.

This patent is subject to a terminal disclaimer.

(21) Appl. No.: 11/606,836

(22) Filed: Nov. 30, 2006

(65) Prior Publication Data

US 2008/0097375 A1    Apr. 24, 2008

Related U.S. Application Data

(63) Continuation-in-part of application No. 11/589,323, filed on Oct. 27, 2006.

(60) Provisional application No. 60/839,741, filed on Aug. 23, 2006.

(51) Int. Cl.
*A61M 1/00* (2006.01)

(52) U.S. Cl. .................. 604/152; 604/131; 604/151

(58) Field of Classification Search .................. 604/131, 604/151, 152, 890.1
See application file for complete search history.

(56) References Cited

U.S. PATENT DOCUMENTS

| | | | |
|---|---|---|---|
| 3,963,151 A | 6/1976 | North, Jr. | |
| 4,064,879 A | 12/1977 | Leibinsohn | |
| 4,089,624 A | 5/1978 | Nichols et al. | |
| 4,447,234 A | * 5/1984 | Mayfield | 604/152 |
| 4,518,384 A | 5/1985 | Tarello et al. | |
| 4,676,122 A | 6/1987 | Szabo et al. | |
| 4,836,496 A | 6/1989 | Abujudom et al. | |
| 4,838,857 A | 6/1989 | Strowe et al. | |
| 4,886,499 A | 12/1989 | Cirelli et al. | |
| 4,976,696 A | 12/1990 | Sanderson et al. | |
| 5,002,527 A | 3/1991 | Reller et al. | |
| 5,053,001 A | 10/1991 | Reller et al. | |
| 5,062,834 A | 11/1991 | Gross et al. | |
| 5,090,963 A | 2/1992 | Gross et al. | |
| 5,156,591 A | 10/1992 | Gross et al. | |

(Continued)

FOREIGN PATENT DOCUMENTS

EP    1 527 792 A1    5/2005

(Continued)

OTHER PUBLICATIONS

PCT Search Report dated Mar. 5, 2008 for PCT/US2007/076466.

(Continued)

*Primary Examiner* — Kevin C Sirmons
*Assistant Examiner* — Emily Schmidt
(74) *Attorney, Agent, or Firm* — Foley & Lardner LLP

(57) ABSTRACT

A delivery device includes a durable housing portion and a separable disposable portion that selectively engage and disengage from each other. The disposable housing portion secures to the patient-user and may be disposed of after it has been in use for a prescribed period. Components that normally come into contact with a patient-user or with an infusion medium, including a pump device, are supported by the disposable housing portion for disposal after the prescribed use, while the durable housing portion supports other components such as electronics for controlling delivery of the infusion medium from the reservoir and a drive device and drive linkage.

36 Claims, 17 Drawing Sheets

U.S. PATENT DOCUMENTS

| | | | |
|---|---|---|---|
| 5,176,502 A | 1/1993 | Sanderson et al. |
| 5,186,805 A | 2/1993 | Gross et al. |
| 5,190,522 A | 3/1993 | Wojcicki et al. |
| 5,203,506 A | 4/1993 | Gross et al. |
| 5,207,666 A | 5/1993 | Idriss et al. |
| 5,232,449 A | 8/1993 | Stern et al. |
| 5,242,406 A | 9/1993 | Gross et al. |
| 5,242,408 A | 9/1993 | Jhuboo et al. |
| 5,246,147 A | 9/1993 | Gross et al. |
| 5,254,096 A | 10/1993 | Rondelet et al. |
| 5,259,732 A | 11/1993 | Stern |
| 5,261,884 A | 11/1993 | Stern et al. |
| 5,295,966 A | 3/1994 | Stern et al. |
| 5,295,967 A | 3/1994 | Rondelet et al. |
| 5,356,632 A | 10/1994 | Gross et al. |
| 5,425,706 A | 6/1995 | Gross et al. |
| 5,527,288 A | 6/1996 | Gross et al. |
| 5,704,520 A | 1/1998 | Gross |
| 5,800,420 A | 9/1998 | Gross et al. |
| 5,807,375 A | 9/1998 | Gross et al. |
| 5,820,622 A | 10/1998 | Gross et al. |
| 5,848,991 A | 12/1998 | Gross et al. |
| 5,851,549 A | 12/1998 | Svec |
| 5,858,001 A | 1/1999 | Tsals et al. |
| 5,871,125 A | 2/1999 | Gross |
| 5,876,189 A | 3/1999 | Lukas et al. |
| 5,933,287 A | 8/1999 | Muller |
| 5,951,523 A | 9/1999 | Osterlind et al. |
| 5,954,697 A | 9/1999 | Srisathapat et al. |
| 5,957,889 A | 9/1999 | Poulsen et al. |
| 5,984,894 A | 11/1999 | Poulsen et al. |
| 5,997,501 A | 12/1999 | Gross et al. |
| 6,003,736 A | 12/1999 | Ljunggren |
| 6,033,377 A | 3/2000 | Rasmussen et al. |
| 6,099,504 A | 8/2000 | Gross et al. |
| 6,179,583 B1 | 1/2001 | Weston |
| 6,186,982 B1 | 2/2001 | Gross et al. |
| 6,229,584 B1 | 5/2001 | Chuo et al. |
| 6,261,272 B1 | 7/2001 | Gross et al. |
| 6,270,478 B1 | 8/2001 | Mernøe |
| 6,275,717 B1 | 8/2001 | Gross et al. |
| 6,312,409 B1 | 11/2001 | Gross |
| 6,314,317 B1 | 11/2001 | Willis |
| 6,346,095 B1 | 2/2002 | Gross et al. |
| 6,364,865 B1 | 4/2002 | Lavi et al. |
| 6,406,455 B1 | 6/2002 | Willis et al. |
| 6,423,035 B1 | 7/2002 | Das et al. |
| 6,440,096 B1 | 8/2002 | Lastovich et al. |
| 6,474,219 B2 | 11/2002 | Klitmose et al. |
| 6,478,771 B1 | 11/2002 | Lavi et al. |
| 6,485,461 B1 | 11/2002 | Mason et al. |
| 6,490,483 B2 | 12/2002 | Willis |
| 6,508,788 B2 | 1/2003 | Preuthun |
| 6,537,251 B2 | 3/2003 | Klitmose |
| 6,585,707 B2 | 7/2003 | Cabiri et al. |
| 6,589,229 B1 | 7/2003 | Connelly et al. |
| 6,595,956 B1 | 7/2003 | Gross et al. |
| 6,607,513 B1 | 8/2003 | Down et al. |
| 6,613,019 B2 | 9/2003 | Munk |
| 6,616,627 B2 | 9/2003 | Willis et al. |
| 6,641,565 B1 | 11/2003 | Lavi et al. |
| 6,645,181 B1 | 11/2003 | Lavi et al. |
| 6,656,158 B2 | 12/2003 | Mahoney et al. |
| 6,656,159 B2 | 12/2003 | Flaherty |
| 6,669,669 B2 | 12/2003 | Flaherty et al. |
| 6,689,100 B2 | 2/2004 | Connelly et al. |
| 6,692,457 B2 | 2/2004 | Flaherty |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,723,068 B2 | 4/2004 | Lavi et al. |
| 6,723,072 B2 | 4/2004 | Flaherty et al. |
| 6,740,059 B2 | 5/2004 | Flaherty |
| 6,749,587 B2 | 6/2004 | Flaherty |
| 6,767,188 B2 | 7/2004 | Vrane et al. |
| 6,768,425 B2 | 7/2004 | Flaherty et al. |
| 6,770,054 B1 * | 8/2004 | Smolyarov et al. ............ 604/140 |
| 6,786,246 B2 | 9/2004 | Ohms et al. |
| 6,808,506 B2 | 10/2004 | Lastovich et al. |
| 6,830,558 B2 | 12/2004 | Flaherty et al. |
| 6,830,560 B1 | 12/2004 | Gross et al. |
| 6,899,699 B2 | 5/2005 | Enggaard |
| 6,916,159 B2 | 7/2005 | Rush et al. |
| 6,936,006 B2 | 8/2005 | Sabra |
| 6,939,324 B2 | 9/2005 | Gonnelli et al. |
| 6,948,918 B2 | 9/2005 | Hansen |
| 6,952,604 B2 | 10/2005 | DeNuzzio et al. |
| 6,960,184 B2 | 11/2005 | Willis et al. |
| 6,960,192 B1 | 11/2005 | Flaherty et al. |
| 6,997,911 B2 | 2/2006 | Klitmose |
| 7,008,399 B2 | 3/2006 | Larsen et al. |
| 7,018,360 B2 | 3/2006 | Flaherty et al. |
| 7,027,478 B2 | 4/2006 | Ackley |
| 7,029,455 B2 | 4/2006 | Flaherty |
| 7,083,592 B2 | 8/2006 | Lastovich et al. |
| 7,083,599 B2 | 8/2006 | Alchas et al. |
| 7,115,108 B2 | 10/2006 | Wilkinson et al. |
| 7,128,727 B2 | 10/2006 | Flaherty et al. |
| 7,133,329 B2 | 11/2006 | Skyggebjerg et al. |
| 7,137,964 B2 | 11/2006 | Flaherty |
| 7,144,384 B2 | 12/2006 | Gorman et al. |
| 7,150,409 B2 | 12/2006 | Gonnelli et al. |
| 7,156,838 B2 | 1/2007 | Gabel et al. |
| 7,187,969 B2 | 3/2007 | Willis |
| 2002/0040208 A1 | 4/2002 | Flaherty et al. |
| 2002/0072733 A1 | 6/2002 | Flaherty |
| 2002/0123740 A1 | 9/2002 | Flaherty et al. |
| 2002/0126036 A1 | 9/2002 | Flaherty et al. |
| 2002/0169439 A1 | 11/2002 | Flaherty |
| 2002/0173774 A1 * | 11/2002 | Olsen ................ 604/891.1 |
| 2003/0055380 A1 | 3/2003 | Flaherty |
| 2003/0073952 A1 | 4/2003 | Flaherty et al. |
| 2003/0097092 A1 | 5/2003 | Flaherty |
| 2003/0167035 A1 | 9/2003 | Flaherty et al. |
| 2003/0167036 A1 | 9/2003 | Flaherty |
| 2003/0198558 A1 | 10/2003 | Nason et al. |
| 2003/0199824 A1 | 10/2003 | Mahoney et al. |
| 2003/0199825 A1 | 10/2003 | Flaherty |
| 2003/0229310 A1 | 12/2003 | Flaherty et al. |
| 2003/0233069 A1 | 12/2003 | Gillespie et al. |
| 2004/0010207 A1 | 1/2004 | Flaherty et al. |
| 2004/0015131 A1 | 1/2004 | Flaherty et al. |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0116866 A1 | 6/2004 | Gorman et al. |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0254526 A1 | 12/2004 | Weston |
| 2004/0260233 A1 | 12/2004 | Garibotto et al. |
| 2005/0020980 A1 * | 1/2005 | Inoue et al. ............... 604/152 |
| 2005/0022274 A1 | 1/2005 | Campbell et al. |
| 2005/0059932 A1 * | 3/2005 | Reilly et al. ............... 604/152 |
| 2006/0264835 A1 | 11/2006 | Nielsen et al. |
| 2007/0134112 A1 * | 6/2007 | Hupp ................... 417/437 |

FOREIGN PATENT DOCUMENTS

| | | |
|---|---|---|
| EP | 1 347 705 | 12/2005 |
| EP | 1 423 079 | 7/2006 |
| EP | 1 135 056 | 8/2006 |
| EP | 1 702 635 | 9/2006 |
| EP | 1 545 657 | 11/2006 |
| EP | 1 546 556 | 12/2006 |
| EP | 1 341 569 | 1/2007 |
| EP | 1 461 070 | 1/2007 |
| EP | 1 464 351 | 1/2007 |
| EP | 1 309 366 | 2/2007 |
| EP | 0 944 648 | 3/2007 |
| EP | 1 646 412 | 3/2007 |
| EP | 1 095 668 | 4/2007 |
| FR | 2 455 269 | 12/1980 |
| GB | 1 452 104 | 10/1976 |
| NL | 1019126 | 4/2003 |
| WO | WO 93/04714 | 3/1993 |

| | | | | | | |
|---|---|---|---|---|---|---|
| WO | WO-99/59665 | 11/1999 | WO | WO 2006/077263 A1 | 7/2006 |
| WO | WO-00/47254 | 8/2000 | WO | WO 2006/084464 A1 | 8/2006 |
| WO | WO 01/76684 A1 | 10/2001 | WO | WO 2006/086980 A1 | 8/2006 |
| WO | WO 02/20073 A2 | 3/2002 | WO | WO 2006/089547 A1 | 8/2006 |
| WO | WO 02/28454 A2 | 4/2002 | WO | WO 2006/089548 A1 | 8/2006 |
| WO | WO 02/40083 A2 | 5/2002 | WO | WO 2006/089965 A1 | 8/2006 |
| WO | WO 02/49509 A2 | 6/2002 | WO | WO 2006/096746 A1 | 9/2006 |
| WO | WO 02/068015 A2 | 9/2002 | WO | WO 2006/097453 A1 | 9/2006 |
| WO | WO-03/006090 A1 | 1/2003 | WO | WO 2006/104806 A2 | 10/2006 |
| WO | WO 03/024504 A2 | 3/2003 | WO | WO 2006/108775 A2 | 10/2006 |
| WO | WO 03/033051 A1 | 4/2003 | WO | WO 2006/108809 A1 | 10/2006 |
| WO | WO 03/059372 A2 | 7/2003 | WO | WO 2006/116997 A1 | 11/2006 |
| WO | WO 03/059372 A3 | 7/2003 | WO | WO 2006/120253 A2 | 11/2006 |
| WO | WO 03/074121 A1 | 9/2003 | WO | WO 2006/125692 A1 | 11/2006 |
| WO | WO 03/090509 A2 | 11/2003 | WO | WO 2007/000425 A2 | 1/2007 |
| WO | WO 03/090819 A2 | 11/2003 | WO | WO 2007/000426 A2 | 1/2007 |
| WO | WO 03/090838 A1 | 11/2003 | WO | WO 2007/000427 A1 | 1/2007 |
| WO | WO 03/103758 A1 | 12/2003 | WO | WO-2007/038091 A2 | 4/2007 |
| WO | WO 03/103763 A1 | 12/2003 | WO | WO-2007/071255 A1 | 6/2007 |
| WO | WO 2004/006981 A2 | 1/2004 | WO | WO-2007/087808 A1 | 8/2007 |
| WO | WO 2004/006982 A2 | 1/2004 | | | |
| WO | WO 2004/030716 A2 | 4/2004 | | | |
| WO | WO 2004/030717 A2 | 4/2004 | | | |
| WO | WO-2004/047641 A2 | 6/2004 | | | |
| WO | WO 2004/060436 A2 | 7/2004 | | | |
| WO | WO 2004/093648 A2 | 11/2004 | | | |
| WO | WO 2004/098390 A2 | 11/2004 | | | |
| WO | WO 2004/098454 A2 | 11/2004 | | | |
| WO | WO-2004/110526 A1 | 12/2004 | | | |
| WO | WO 2005/037350 A2 | 4/2005 | | | |
| WO | WO-2005/094920 A1 | 10/2005 | | | |
| WO | WO 2006/015922 A1 | 2/2006 | | | |
| WO | WO 2006/018425 A2 | 2/2006 | | | |
| WO | WO 2006/018425 A3 | 2/2006 | | | |
| WO | WO 2006/018447 A2 | 2/2006 | | | |
| WO | WO 2006/018447 A3 | 2/2006 | | | |
| WO | WO 2006/024671 A1 | 3/2006 | | | |
| WO | WO 2006/024672 A1 | 3/2006 | | | |
| WO | WO-2006/032692 A1 | 3/2006 | | | |
| WO | WO 2006/042811 A2 | 4/2006 | | | |
| WO | WO 2006/042811 A3 | 4/2006 | | | |
| WO | WO 2006/072416 A2 | 7/2006 | | | |
| WO | WO 2006/075016 A1 | 7/2006 | | | |
| WO | WO 2006/077262 A1 | 7/2006 | | | |

OTHER PUBLICATIONS

Partial PCT Search Report dated Jan. 24, 2008 for PCT/US2007/076466.

International Search Report dated Feb. 29, 2008 for PCT Application PCT/US2007/076474.

Office Action Dated Jun. 17, 2009 from related U.S. Appl. No. 11/589,323.

Office Action dated Sep. 22, 2009 from related U.S. Appl. No. 11/589,323.

Partial International Search Report dated Jan. 2, 2008 for PCT application PCT/US2007/076474.

US Office Action on dated Oct. 4, 2010 from related patent U.S. Appl. No. 11/606,703.

US Office Action dated Mar. 9, 2011 from related patent U.S. Appl. No. 11/606,703.

Office Action dated Mar. 23, 2010 from related U.S. Appl. No. 11/589,323.

* cited by examiner

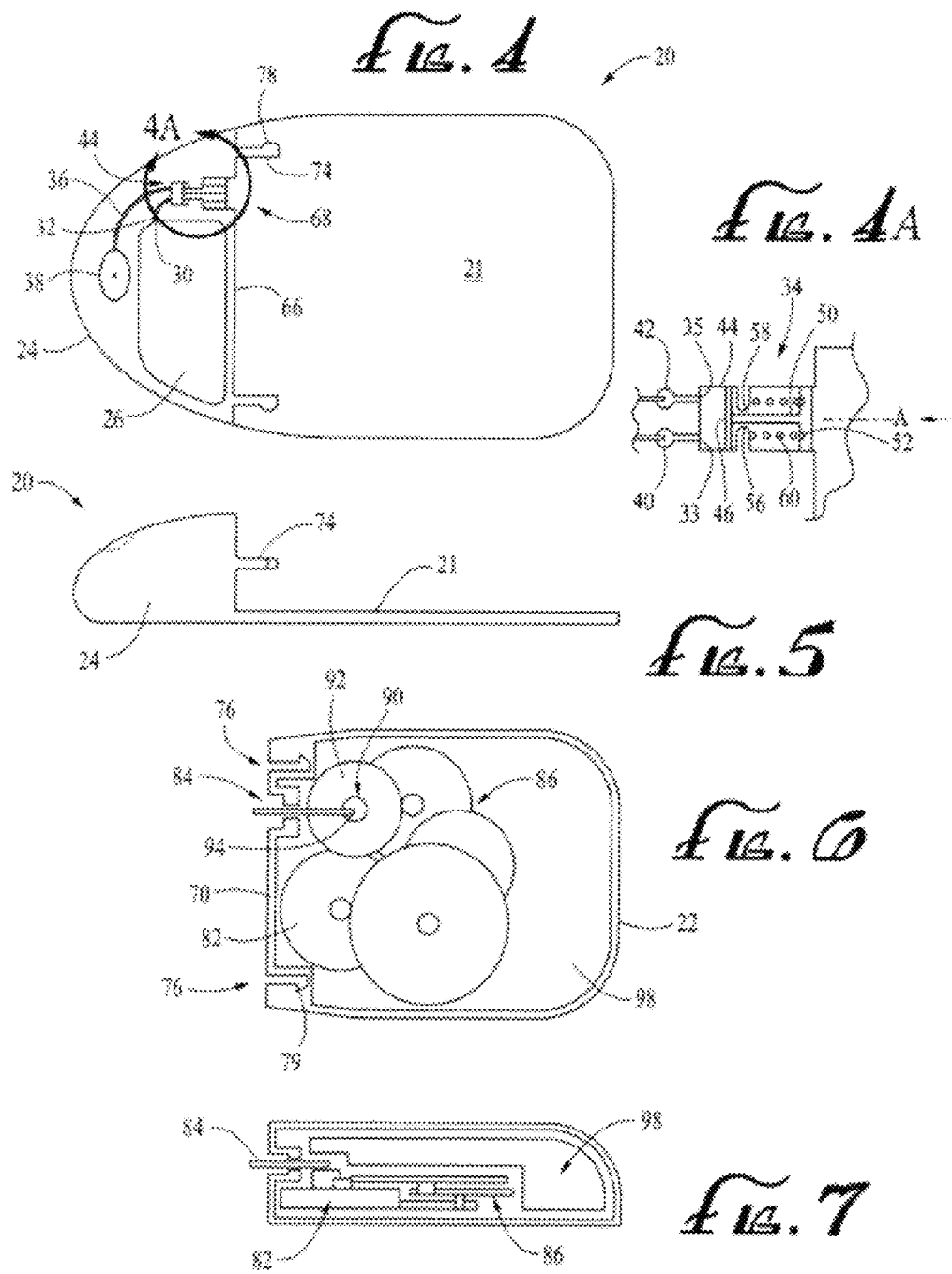

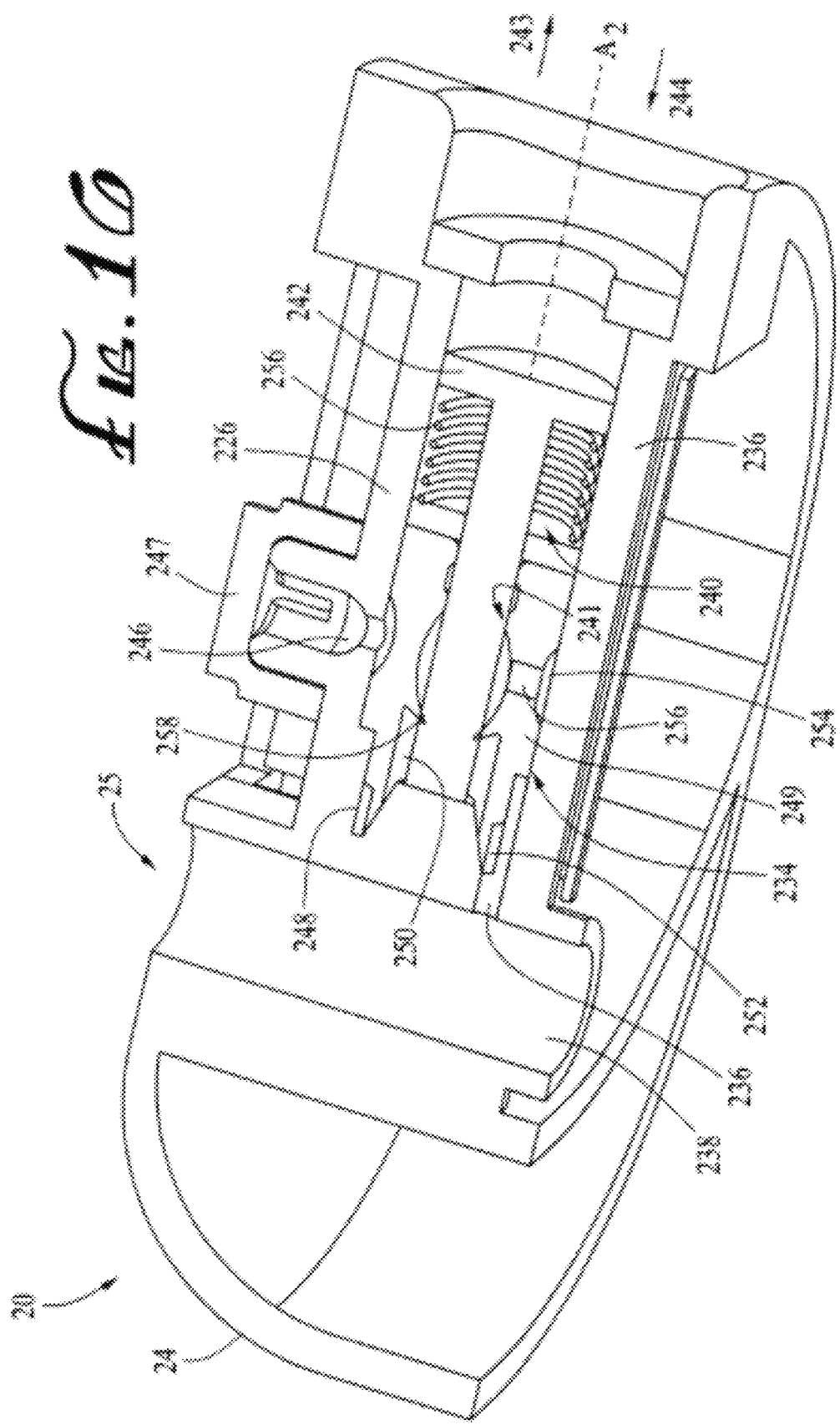

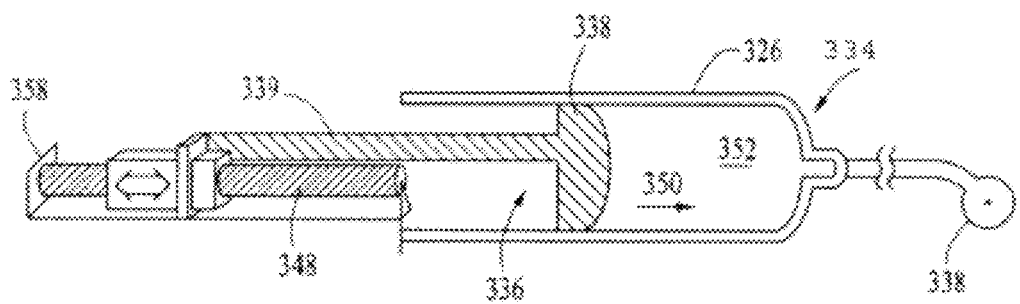
FIG. 19
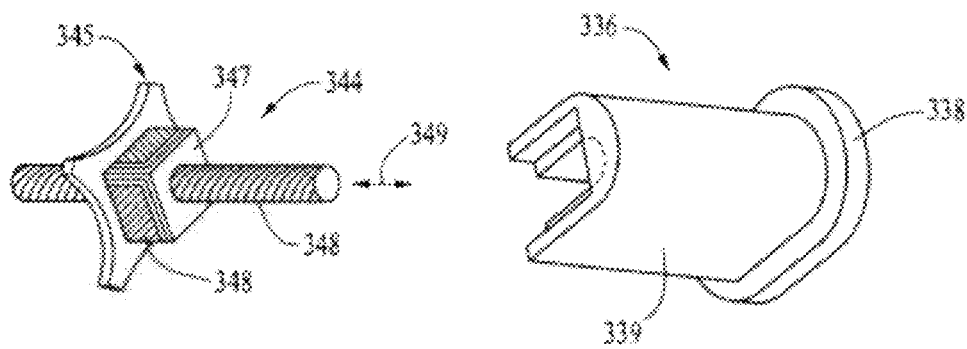
FIG. 18
FIG. 20
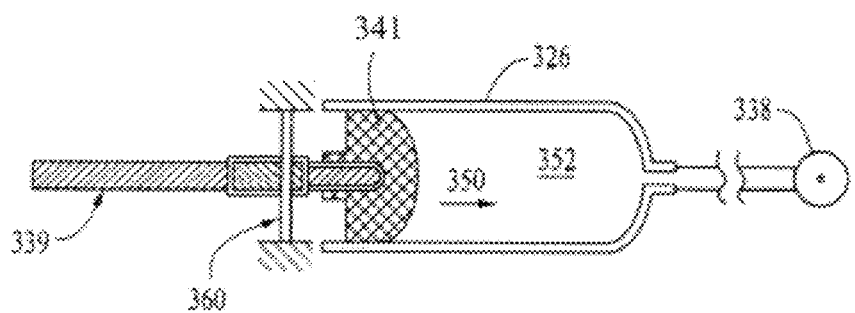
FIG. 21

INFUSION PUMPS AND METHODS AND DELIVERY DEVICES AND METHODS WITH SAME

CROSS-REFERENCE TO RELATED PATENT APPLICATIONS

The present application is a Continuation-In-Part of U.S. patent application Ser. No. 11/589,323, filed, Oct. 27, 2006, titled "Infusion Pumps And Methods And Delivery Devices And Methods With Same", which is incorporated herein by reference, in its entirety. In addition, the present invention relates to U.S. Application 60/839,741, filed Aug. 23, 2006, titled "Infusion Pumps And Methods And Delivery Devices And Methods With Same," which is incorporated herein by reference in its entirety and from which a priority filing date is claimed. The present invention also relates to U.S. Patent Application No. 60/678,290, filed May 6, 2005 and U.S. patent application Ser. No. 11/211,095, filed Aug. 23, 2005, titled "Infusion Device And Method With Disposable Portion," each of which is incorporated herein by reference in its entirety and from which the priority filing date is claimed. The present invention also relates to co-pending U.S. patent application No. 60/839,821, filed Aug. 23, 2006, titled "Infusion Medium Delivery Device And Method For Driving Plunger In Reservoir"; co-pending U.S. patent application No. 60/839,822, filed Aug. 23, 2006, titled "Infusion Medium Delivery Device And Method For Driving Plunger In Reservoir"; co-pending U.S. patent application No. 60/839,832, filed Aug. 23, 2006, titled "Infusion Medium Delivery Device With Compressible Or Curved Reservoir Or Conduit"; and co-pending U.S. patent application No. 60/839,840, filed Aug. 23, 2006, titled "Infusion Medium Delivery Device, System And Method With Needle Inserter And Needle Inserter Device And Method", the contents of each of which is incorporated herein by reference, in its entirety. Embodiments of the present invention also relate to: (i) U.S. patent application Ser. No. 11/588,832, filed Oct. 27, 2006, entitled "Infusion Medium Delivery Device and Method with Drive Device for Driving Plunger in Reservoir"; (ii) U.S. patent application Ser. No. 11/588,847, filed Oct. 27, 2006, entitled "Infusion Medium Delivery Device and Method with Compressible or Curved Reservoir or Conduit"; (iii) U.S. Provisional Patent Application Ser. No. 60/854,829, filed Oct. 27, 2006, entitled "Infusion Medium Delivery System, Device and Method with Needle Inserter and Needle Inserter Device and Method"; and (iv) U.S. patent application Ser. No. 11/588,875, filed Aug. 23, 2006, entitled "Systems And Methods Allowing For Reservoir Filling And Infusion Medium Delivery", (v) U.S. patent application Ser. No. 11/602,173, filed Nov. 20, 2006, entitled "Systems and Methods Allowing for Reservoir filling and Infusion Medium Delivery"; (vi) U.S. patent application Ser. No. 11/602,052, filed Nov. 20, 2006, entitled "Systems and Methods Allowing for Reservoir filling and Infusion Medium Delivery"; (vii) U.S. patent application Ser. No. 11/602,428, filed Nov. 20, 2006, entitled "Systems and Methods Allowing for Reservoir filling and Infusion Medium Delivery"; (viii) U.S. patent application Ser. No. 11/602,113, filed Nov. 20, 2006, entitled "Systems and Methods Allowing for Reservoir filling and Infusion Medium Delivery"; (ix) U.S. patent application Ser. No. 11/604,172, filed Nov. 22, 2006, entitled "Infusion Medium Delivery Device and Method and Drive Device for Driving Plunger in Reservoir"; (x) U.S. patent application Ser. No. 11/604,171, filed Nov. 22, 2006, entitled "Infusion Medium Delivery Device and Method and Drive Device for Driving Plunger in Reservoir", the contents of each of which are incorporated by reference herein, in their entirety.

Embodiments of the present invention relate to an infusion medium delivery device for delivering an infusion medium to a patient-user, wherein the delivery device includes a base portion and a durable portion connectable to the base portion, and wherein the base portion can be separated from the durable portion and disposed of after one or more specified number of uses. The base portion supports a reservoir, while the durable portion supports a drive device that is operatively coupled to the reservoir, to selectively drive fluid out of the reservoir.

BACKGROUND OF THE INVENTION

Certain chronic diseases may be treated, according to modern medical techniques, by delivering a medication or other substance to a patient's body, either in a continuous manner or at particular times or time intervals within an overall time period. For example, diabetes is a chronic disease that is commonly treated by delivering defined amounts of insulin to the patient at appropriate times. Some common modes of providing an insulin therapy to a patient include delivery of insulin through manually operated syringes and insulin pens. Other modern systems employ programmable pumps to deliver controlled amounts of insulin to a patient.

Pump type delivery devices have been configured in external devices (that connect to a patient-user) or implantable devices (to be implanted inside of a patient-user's body). External pump type delivery devices include devices designed for use in a generally stationary location (for example, in a hospital or clinic), and further devices configured for ambulatory or portable use (to be carried by a patient-user). Examples of some external pump type delivery devices are described in U.S. patent application Ser. No. 11/211,095, filed Aug. 23, 2005, titled "Infusion Device And Method With Disposable Portion" and Published PCT Application WO 01/70307 (PCT/US01/09139) titled "Exchangeable Electronic Cards For Infusion Devices" (each of which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a patient-user, for example, through a suitable hollow tubing. The hollow tubing may be connected to a hollow needle that is designed to pierce the patient-user's skin and deliver an infusion medium to the patient-user. Alternatively, the hollow tubing may be connected directly to the patient-user as or through a cannula.

In contexts in which the hollow tubing is connected to the patient-user through a hollow needle that pierces the patient-user's skin, a manual insertion of the needle into the patient-user can be somewhat traumatic to the patient-user. Accordingly, insertion mechanisms have been made to assist the insertion of a needle into the patient-user, whereby a needle is forced by a spring to quickly move from a retracted position into an extended position. Examples of insertion mechanisms that are built into a delivery device are described in U.S. patent application Ser. No. 11/211,095, filed Aug. 23, 2005, titled "Infusion Device And Method With Disposable Portion" (assigned to the assignee of the present invention), which is incorporated herein by reference in its entirety. Other examples of insertion tools are described in U.S. Patent Application Publication No. 2002/0022855, titled "Insertion Device For An Insertion Set And Method Of Using The Same" (assigned to the assignee of the present invention), which is incorporated herein by reference in its entirety. As the needle is moved into the extended position, the needle is quickly forced through the patient-user's skin in a single, relatively abrupt motion that can be less traumatic to a patient-user as compared to a slower, manual insertion of a needle.

As compared to syringes and insulin pens, pump type delivery devices can be significantly more convenient to a patient-user, in that accurate doses of insulin may be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and doctors and patient-users become more familiar with such devices, the popularity of external medical infusion pump treatment increases and is expected to increase substantially over the next decade.

SUMMARY OF THE DISCLOSURE

Embodiments of the present invention relate, generally, to delivery devices, systems and methods for delivering an infusion medium to a recipient, such as a medical patient. Such delivery devices may include first and second housing portions (referred to herein as a durable housing portion and a disposable housing portion, respectively) that are configured to engage and attach to each other for operation. The disposable housing portion may contain an infusion medium reservoir and other components that come into contact with the infusion medium and/or the patient-user during operation. The disposable housing portion may also contain a pump device in accordance with one of the embodiments described herein. The durable housing portion may contain or otherwise support components that do not come into contact with the infusion medium or the patient-user during normal operation of the delivery device, including, but not limited to, a drive device, drive linkage, electronic circuits and, in some embodiments, a power source.

The disposable housing portion may be disengaged and separated from the durable housing portion, such that the disposable housing portion may be readily disposed of after it has been in use for a period of time, or after one or a prescribed number of uses. After disengagement and separation from a disposable housing portion, the durable housing portion may be engaged and operatively connected to another disposable housing portion (such as a new, refurbished, user-filled, prefilled, refilled or re-manufactured disposable housing portion) for further operation.

Thus, a delivery device for delivering an infusion medium to a user according to example embodiments of the invention may include a disposable housing portion adapted to be secured to a user and a durable housing portion configured to be selectively engaged with and disengaged from the disposable housing portion, to allow disposal of the disposable housing portion without disposing of the durable housing portion. Delivery device embodiments described herein may employ any one of various pump embodiments described herein, to draw the infusion medium from the reservoir and/or convey the infusion medium to an injection site.

For example, a delivery device as described herein may include a pump device supported by the disposable housing portion and arranged to be operatively driven by a drive device, through a drive shaft. The drive shaft may be supported by the durable housing portion, for movement in a first direction and in a second direction opposite to the first direction. The drive device may operatively connect to the drive shaft, to selectively move the drive shaft in the first direction to drive the pump device.

The pump device according to an embodiment of the invention is provided with a piston chamber having an interior including a fluid portion having a variable volume for containing an infusion medium. An inlet port of the pump device is provided in fluid flow communication with the interior volume of the piston chamber. The inlet port is configured for connection with a reservoir, for fluid flow communication with the reservoir.

An outlet port of the pump device is provided in fluid flow communication with interior volume of the piston chamber. A push plate is supported for back-and-forth movement in a first direction and in a second direction opposite to the first direction, where the push plate is arranged in a position for operative engagement with the drive shaft to move the push plate in the first direction as the drive shaft is moved in the first direction, and to allow movement of the push plate in the second direction as the drive shaft is moved in the second direction, when the disposable housing portion and the durable housing portion are engaged with each other.

A piston head is supported for movement within the piston chamber between a retracted position and an active position to vary the volume of the fluid portion of the piston chamber. The piston head is operatively coupled in a fixed relation to the push plate, for movement from the retracted position to the active position with movement of the push plate in the first direction. When the piston chamber contains infusion fluid, the volume of the fluid portion of the piston chamber is reduced as the piston head is moved from the retracted position to the active position to provide a pressure within the piston chamber to force the infusion fluid from the fluid portion of the piston chamber and through the outlet port. Conversely, the volume of the fluid portion of the piston chamber is increased as the piston head is moved from the retracted position to the active position to provide a pressure within the piston chamber to draw infusion fluid into the fluid portion of the piston chamber, through the inlet port, when the inlet port is connected in fluid flow communication with a reservoir.

The delivery device according to an embodiment of the invention includes a bias member operatively coupled to the push plate, for imparting a bias force on the push plate in the second direction sufficient to move the push plate in the second direction as the drive shaft is moved in the second direction, when the disposable housing portion and the durable housing portion are engaged with each other. In the same or further embodiments, the push plate is coupled to the piston head by a piston rod and the piston chamber is open to a channel section through which the piston rod extends. A seal is provided to inhibit fluid from passing through the channel section.

In the same or further embodiments, the delivery device includes a reservoir having an interior volume for containing an infusion medium and a conduit connecting the interior volume of the reservoir in fluid flow communication with the inlet port of the pump device. The reservoir may be supported by the disposable housing portion.

According to example embodiments, the disposable housing portion includes a housing structure that has an interior volume in which the pump device is located. Also, the housing structure of the disposable housing portion includes a wall having an opening. The push plate has a surface that is positioned to be acted upon by the drive shaft, through the opening in the wall of the housing structure of the disposable housing portion, when the disposable housing portion and the durable housing portion are engaged with each other.

According to further example embodiments, the durable housing portion includes a housing structure having an interior volume in which the drive device is located. Also, the housing structure of the durable housing portion includes a wall having an opening through which the drive shaft extends. The drive shaft has an end that is positioned external to the durable housing portion for engaging the surface of the push plate, when the disposable housing portion and the durable housing portion are engaged with each other.

According to another aspect of the invention, a pump device is provided for conveying an fluidic medium. The pump device has a piston chamber having an interior that includes a fluid portion having a variable volume for containing a fluidic medium. An inlet port is provided in fluid flow communication with the interior volume of the piston chamber. The inlet port is configured for connection with a source of fluidic medium, for receiving fluid medium from the source into the interior volume of the piston chamber. An outlet port is provided in fluid flow communication with interior volume of the piston chamber.

In the above pump embodiment, a push plate is supported for back-and-forth movement in a first direction and in a second direction opposite to the first direction. The push plate is arranged in a position for operative engagement with a drive shaft for movement of the push plate in the first direction as the drive shaft is moved in the first direction, and for allowing movement of the push plate in the second direction as the drive shaft is moved in the second direction. A piston head is supported for movement within the piston chamber between a retracted position and an active position to vary the volume of the fluid portion of the piston chamber. The piston head is operatively coupled in a fixed relation to the push plate, for movement from the retracted position to the active position with movement of the push plate in the first direction.

When the piston chamber contains infusion fluid, the volume of the fluid portion of the piston chamber is reduced as the piston head is moved from the retracted position to the active position to provide a pressure within the piston chamber to force the infusion fluid from the fluid portion of the piston chamber and through the outlet port. The volume of the fluid portion of the piston chamber is increased as the piston head is moved from the retracted position to the active position to provide a pressure within the piston chamber to draw a fluidic medium into the fluid portion of the piston chamber, through the inlet port, when the inlet port is connected in fluid flow communication with the source of fluidic medium.

The pump device according to an embodiment of the invention has a bias member operatively coupled to the push plate, for imparting a bias force on the push plate in the second direction sufficient to move the push plate in the second direction as the drive shaft is moved in the second direction, when the disposable housing portion and the durable housing portion are engaged with each other. In the same or further embodiments, the push plate is coupled to the piston head by a piston rod and the piston chamber is open to a channel section through which the piston rod extends. A seal is provided to inhibit fluid from passing through the channel section.

Further embodiments of the present invention relate to methods of making a delivery device for delivering an infusion medium to a user. A method according to an embodiment of the invention includes providing a disposable housing portion adapted to be secured to a user and providing a durable housing portion configured to be selectively engaged with and disengaged from the disposable housing portion to allow disposal of the disposable housing portion without disposing of the durable housing portion. The method further includes supporting a drive shaft on the durable housing portion for movement in a first direction and in a second direction opposite to the first direction, operatively connecting a drive device to the drive shaft, to selectively move the drive shaft in the first direction, and supporting a pump device on the disposable housing portion.

Supporting the pump device includes providing a piston chamber having an interior including a fluid portion having a variable volume for containing an infusion medium, connecting an inlet port in fluid flow communication with the interior volume of the piston chamber, the inlet port configured for connection with a reservoir, for fluid flow communication with the reservoir and connecting an outlet port in fluid flow communication with interior volume of the piston chamber. In addition, supporting the pump device includes supporting a push plate for back-and-forth movement in a first direction and in a second direction opposite to the first direction, and arranging the push plate in a position for operative engagement with the drive shaft for movement of the push plate in the first direction as the drive shaft is moved in the first direction, and for allowing movement of the push plate in the second direction as the drive shaft is moved in the second direction, when the disposable housing portion and the durable housing portion are engaged with each other.

Supporting the pump device further includes arranging a piston head within the piston chamber for movement between a retracted position and an active position to vary the volume of the fluid portion of the piston chamber, and coupling the piston head in a fixed relation to the push plate, for movement from the retracted position to the active position with movement of the push plate in the first direction. In such a method, when the piston chamber contains infusion fluid, the volume of the fluid portion of the piston chamber is reduced as the piston head is moved from the retracted position to the active position to provide a pressure within the piston chamber to force the infusion fluid from the fluid portion of the piston chamber and through the outlet port. In addition, the volume of the fluid portion of the piston chamber is increased as the piston head is moved from the retracted position to the active position to provide a pressure within the piston chamber to draw infusion fluid into the fluid portion of the piston chamber, through the inlet port, when the inlet port is connected in fluid flow communication with a reservoir.

A method according to further embodiments of the invention includes coupling a bias member to impart a bias force on the push plate in the second direction sufficient to move the push plate in the second direction as the drive shaft is moved in the second direction, when the disposable housing portion and the durable housing portion are engaged with each other. In the same or further embodiments, the method includes providing a reservoir having an interior volume for containing an infusion medium and connecting a conduit in fluid flow communication with the interior volume of the reservoir and with the inlet port of the pump device. The reservoir may be supported on the disposable housing portion.

Supporting a push plate, according to embodiments of the invention, includes coupling the push plate to the piston head by a piston rod, extending the piston rod through an opening in the piston chamber to a channel section, and providing a seal to inhibit fluid from passing through the channel section. The method according to the same or further embodiments includes locating the pump device in an interior volume of the disposable housing portion, providing an opening in a wall of the disposable housing portion and arranging a surface of the push plate in a position to be acted upon by the drive shaft, through the opening in the wall of the housing structure of the disposable housing portion, when the disposable housing portion and the durable housing portion are engaged with each other.

The method according to the same or further embodiments includes locating the drive device in an interior volume of the durable housing portion, providing an opening in a wall of the durable housing portion, and extending the drive shaft through the opening in the wall of the durable housing portion. In such embodiments, the drive shaft has an end that is positioned external to the durable housing portion for engaging the surface of the push plate, when the disposable housing portion and the durable housing portion are engaged with each other.

The method according to any of the embodiments described herein may include providing one of the durable housing portion and the disposable housing portion with at least one flexible pawl and the other of the durable housing portion and the disposable housing portion with at least one receptacle having a shape for receiving the at least one flexible pawl, when the disposable housing portion and the durable housing portion are engaged with each other. The method according to any of the embodiments described herein may also include containing electrical control circuitry in the durable housing portion, wherein the electrical control circuitry controls the drive device for delivery of the infusion medium from the reservoir to the user when the durable housing portion and the disposable housing portion are engaged. The method according to any of the embodiments described herein may include securing the bottom surface of at least one of the disposable housing portion and the durable housing portion to the skin of a user, for example, by applying an adhesive material to a bottom surface of at least one of the disposable housing portion and the durable housing portion for securing the disposable housing portion or the durable housing portion to the skin of the user. The method may further include providing an injection site at which a hollow needle or cannula may be inserted into a user's skin when the bottom surface of the base portion is secured to the user's skin, and connecting a conduit in fluid flow communication with the hollow needle or cannula and the outlet port of the pump device. Further embodiments include connecting a one-way valve within the conduit. Yet further embodiments include connecting a conduit to the inlet port of the pump device, and connecting a one-way valve within the conduit.

A further example of a delivery device described herein includes a pump device according to an embodiment of the present invention, supported by the disposable housing portion and arranged to be operatively driven by a drive shaft, where the drive shaft is supported by the durable housing portion, for movement in a first direction and in a second direction opposite to the first direction. The delivery device may also include a drive device operatively connected to the drive shaft, to selectively move the drive shaft in the first direction to drive the pump device.

A pump device according to an embodiment of the invention includes a housing provided with a piston channel that has a generally linear, longitudinal axis. The housing also has an inlet port in fluid flow communication with the channel and configured for connection to a reservoir, and an outlet port in fluid flow communication with the channel and configured for connection in fluid flow communication with an injection site. A piston is located in the piston channel and has a first piston section and a second piston section coupled together for limited movement, relative to each other. The second piston section has a surface for operable engagement with the drive shaft when the durable housing portion and disposable hosing portion are engaged.

The piston is moveable with movement of the drive shaft along the longitudinal axis of the piston channel between fill, pull and dispense positions. In the fill position, the first and second piston sections are separate to form a chamber having volume between the first and second piston sections, and the chamber is aligned in fluid flow communication with the inlet port. In the pull position, the first and second piston sections are separated and the chamber formed between the first and second piston sections is located within the channel, between the inlet port and the outlet port, out of fluid flow communication with the inlet port and the outlet port. In the dispense position, the chamber between the first and second piston sections is aligned in fluid flow communication with the outlet port.

The delivery device according to a further embodiment of the invention also includes a reservoir that has an interior volume for containing an infusion medium. A conduit connects the interior volume of the reservoir in fluid flow communication with the inlet port of the housing of the pump device. The reservoir may be supported by the disposable housing portion.

In any of the above-described embodiments, each of the first and second piston sections may have an end surface that faces the end surface of the other of the first and second piston sections. In such embodiments, the second piston section has a hollow interior portion and an opening on one end, into the hollow interior portion. The hollow interior portion of the second piston section has a stop surface. The first piston section includes an extension portion that extends into the hollow interior portion of the second piston section and has a stop surface for engaging the stop surface of the hollow interior portion of the second piston section when the end surfaces of the first and second piston sections are fully separated and the piston is in the fill position. Alternatively, the first piston section may have the hollow interior portion and an opening on one end, into the hollow interior portion, where the hollow interior portion has a stop surface, while the second piston section includes an extension portion extending into the hollow interior portion of the first piston section, where the extension portion has a stop surface for engaging the stop surface of the hollow interior portion of the first piston section when the end surfaces of the first and second piston sections are fully separated and the piston is in the fill position.

As described above, in any of the above-described embodiments, each of the first and second piston sections may have an end surface that faces the end surface of the other of the first and second piston sections. In addition, the end surfaces of the first and second piston sections are arranged to abut each other when the piston is in the dispense position.

Also in any of the above-described embodiments, the second piston section may have an end surface facing away from the first piston section. In such an embodiment, the disposable housing portion includes a housing structure having an interior volume in which the pump device is located and also includes a wall with an opening. The surface of the second piston section that is for operable engagement with the drive shaft is the end surface of the second piston section that faces away from the first piston section, and is positioned to be acted upon by the drive shaft, through the opening in the wall of the housing structure of the disposable housing portion when the disposable housing portion and the durable housing portion are engaged with each other.

In such an embodiment, the durable housing portion may include a housing structure having an interior volume in which the drive device is located and a wall having an opening. The drive shaft extends through the opening in the wall of the durable housing portion. Also in such an embodiment, the drive shaft may have an end that is positioned external to the durable housing portion for operable connection with the end surface of the second piston section, when the disposable housing portion and the durable housing portion are engaged with each other.

Further embodiments of methods of making a pump device for conveying a fluidic medium include providing a piston channel in a housing, where the piston channel has a generally linear, longitudinal axis, providing an inlet port in fluid flow communication with the piston channel and configured for connection to a source of fluidic medium, and providing an outlet port in fluid flow communication with the piston channel. Such methods further include providing a piston having a first piston section and a second piston section coupled together for limited movement, relative to each other, the second piston section having a surface for receiving a drive force from a drive shaft, and supporting the piston within the piston channel for movement along the longitudinal axis of the piston channel between fill, pull and dispense positions, when a drive force is received from a drive shaft. In the fill position, the first and second piston sections are separate to form a chamber having volume between the first and second piston sections, and the chamber is aligned in fluid flow communication with the inlet port. In pull positions, the first and second piston sections are separated and the chamber formed between the first and second piston sections is located within the channel, between the inlet port and the outlet port, out of fluid flow communication with the inlet port and the outlet port. In the dispense position, the chamber between the first and second piston sections is aligned in fluid flow communication with the outlet port. The end surfaces of the first and second piston sections may be arranged to abut each other when the piston is in the dispense position.

According to further embodiments of such methods, supporting the piston within the piston channel includes arranging each of the first and second piston sections end-to-end, with an end surface of each piston section facing an end surface of the other piston section. In addition, providing a piston having first and second piston sections includes providing the second piston section with a hollow interior portion and an opening on one end, into the hollow interior portion, the hollow interior portion having a stop surface and providing the first piston section with an extension portion extending into the hollow interior portion of the second piston section, the extension portion having a stop surface for engaging the stop surface of the hollow interior portion of the second piston section when the end surfaces of the first and second piston sections are fully separated and the piston is in the fill position. Alternatively, providing a piston having first and second piston sections may include providing the first piston section with a hollow interior portion and an opening on one end, into the hollow interior portion, the hollow interior portion having a stop surface and providing the second piston section with an extension portion extending into the hollow interior portion of the first piston section, the extension portion having a stop surface for engaging the stop surface of the hollow interior portion of the first piston section when the end surfaces of the first and second piston sections are fully separated and the piston is in the fill position.

Further method embodiments also include providing a disposable housing portion with a surface adapted to be secured to a user and providing the disposable housing portion and a durable housing portion with connection structure to allow the disposable housing portion and the durable housing portion to be selectively engaged with each other for operation and disengaged from each other to allow disposal of the disposable housing portion without disposing of the durable housing portion. Such methods further include supporting a drive shaft with the durable housing portion, for movement in a generally linear dimension and operatively connecting a drive device to the drive shaft, to selectively move the drive shaft in the generally linear dimension. Such methods further include supporting a pump housing with the disposable housing portion, where the pump housing has a piston channel with a generally linear, longitudinal axis.

Also, such further methods include providing an inlet port extending to the piston channel and configured for connection to a source of fluidic medium and providing an outlet port in fluid flow communication with the piston channel. In addition, such methods include providing a piston having a surface for receiving a drive force from the drive shaft when the disposable housing portion and the durable housing portion are engaged for operation, and supporting the piston in the piston channel for movement along the longitudinal axis of the piston channel between fill and dispense positions upon receiving a force from a drive shaft. In the fill position, the piston is moved to a position to allow fluid flow communication through the inlet port and into the piston channel and piston chamber. In the dispense position, the piston is moved to a position to obstruct fluid flow communication through the inlet port and to reduce the volume of the piston chamber to force fluid in the piston chamber out of the outlet port.

In yet further embodiments, a method includes providing the housing of the pump device with an outlet chamber in fluid flow communication with the piston chamber and the outlet port. Such embodiments further include arranging a one-way valve between the piston chamber and the outlet chamber and arranged to allow fluid flow from the piston chamber to the outlet chamber and inhibit fluid flow from the outlet chamber to the piston chamber. In further embodiments, the one-way valve is a duckbill valve structure.

A pump device according to another embodiment of the invention also includes a housing provided with a piston channel that has a generally linear, longitudinal axis. An inlet port extends to the piston channel and is configured for connection to a reservoir. A piston chamber is in fluid flow communication with the channel. An outlet port is also in fluid flow communication with the piston channel and is configured for connection in fluid flow communication with an injection site.

A piston is located in the piston channel and has a surface for receiving a drive force from the drive shaft when the durable housing portion and disposable hosing portion are engaged. The piston is moveable with movement of the drive shaft along the longitudinal axis of the piston channel between fill and dispense positions. In the fill position, the piston is moved to a position to allow fluid flow communication through the inlet port and into the piston channel and piston chamber. In the dispense position, the piston is moved to a position to obstruct fluid flow communication through the inlet port and to reduce the volume of the piston chamber to force fluid in the piston chamber out of the outlet port.

In further embodiments, the housing of the pump device includes an outlet chamber in fluid flow communication with the piston chamber and the outlet port. In such embodiments, the pump device includes a one-way valve between the piston chamber and the outlet chamber, arranged to allow fluid flow from the piston chamber to the outlet chamber and inhibit fluid flow from the outlet chamber to the piston chamber. In one embodiment, the one-way valve is a duckbill valve structure.

Any of the above-described embodiments may include a reservoir having an interior volume for containing an infusion medium and a conduit connecting the interior volume of the reservoir in fluid flow communication with the inlet port of the housing of the pump device. The reservoir may be supported by the disposable housing portion.

Also in any of the above-described embodiments, the durable housing portion may include a housing structure that has an interior volume in which the drive device is located and a wall having an opening. In such embodiments, the drive shaft extends through the opening in the wall of the durable housing portion. In further embodiments, the drive shaft has an end that is positioned external to the durable housing portion for operable connection with the surface of the piston, when the disposable housing portion and the durable housing portion are engaged with each other.

Also in any of the above-described embodiments, one of the durable housing portion and the disposable housing portion may have at least one flexible pawl and the other of the durable housing portion and the disposable housing portion may have at least one receptacle with a shape for receiving the at least one flexible pawl, when the disposable housing portion and the durable housing portion are engaged with each other. In such embodiments, each flexible pawl may include a first stop surface and each receptacle may include a second stop surface arranged such that the first stop surface engages the second stop surface, upon the pawl being received within the receptacle.

Also in any of the above-described embodiments, electrical control circuitry may be contained in the durable housing portion. The electrical control circuitry controls the drive device for delivery of the infusion medium from the reservoir to the user when the durable housing portion and the disposable housing portion are engaged.

Also in any of the above-described embodiments, the base portion has a bottom surface and an adhesive material may be provided on the bottom surface for securing the disposable housing portion to the skin of the user. Further embodiments may include an injection site at which a hollow needle or cannula may be inserted into a user's skin when the bottom surface of the base portion is secured to the user's skin, and a conduit that couples the injection site in fluid flow communication with the outlet port of the pump device. In yet further embodiments, a one-way valve is provided within the conduit. In yet further embodiments, a conduit is coupled to the inlet port of the pump device, and a one-way valve within the conduit.

In any of the above-described embodiments, a conduit may be coupled to the inlet port of the pump device, and a one-way valve may be provided within the conduit. These and other embodiments of the invention are described herein with reference to the accompanying drawings.

BRIEF DESCRIPTION OF THE DRAWINGS

FIG. 4 is a schematic, cross-sectional view of a disposable housing portion of a delivery device according to an embodiment of the invention.

FIG. 5 is a side view of the disposable housing portion of the embodiment of FIG. 4.

FIG. 6 is a schematic, cross-sectional view of a durable housing portion of a delivery device according to an embodiment of the invention.

FIG. 7 is a side, schematic, cross-sectional view of the durable housing portion of FIG. 6.

FIGS. 16 and 17 each show a side cross section view of pump device according to another embodiment of the invention, with the piston in the extended and retracted positions, respectively.

FIG. 18 shows a perspective view of a linear motion motor that may be employed in a further embodiment of the invention.

FIG. 19 shows a schematic, cross-section view of a pump device and reservoir according to a further embodiment of the invention that employs a motor of FIG. 18.

FIG. 20 is a perspective view of a piston plunger for the embodiment of FIG. 19.

FIG. 21 shows a schematic, cross-section view of a pump device and reservoir according to yet a further embodiment of the invention that employs a motor of FIG. 18.

DETAILED DESCRIPTION

Figure 1:
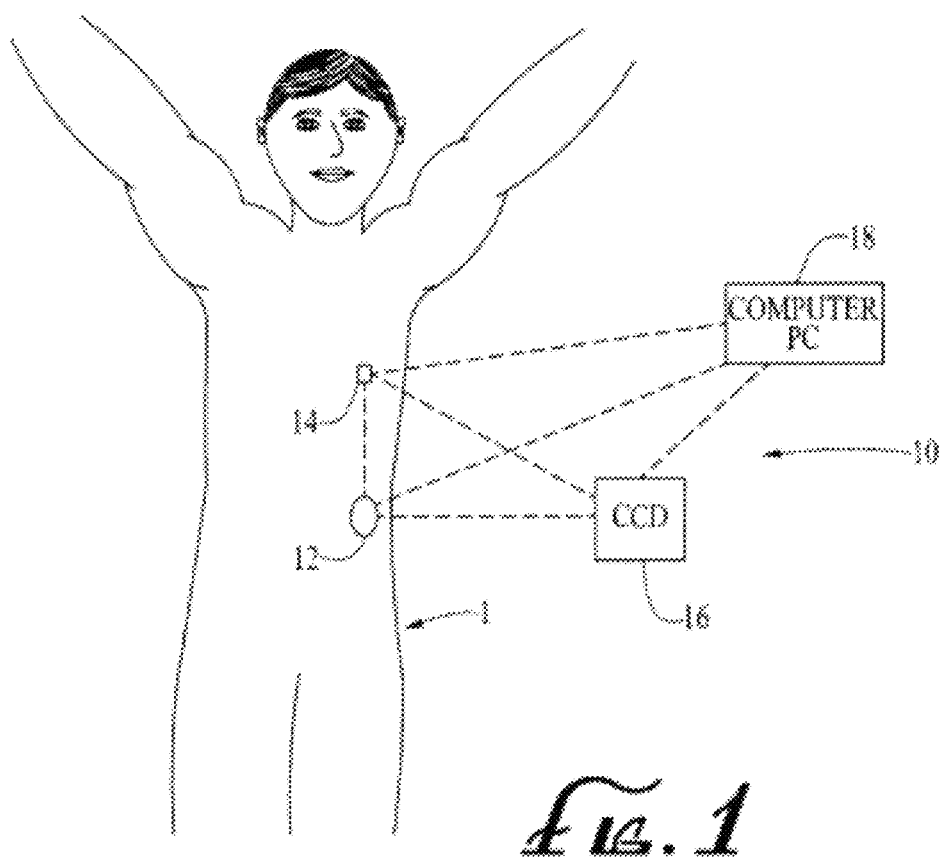
FIG. 1 is a generalized diagram of a delivery system in relation to a human patient-user.

The present invention relates, generally, to delivery devices, systems and methods for delivering an infusion medium, such as a drug, to a recipient, such as a medical patient. In particular embodiments, a delivery device includes first and second housing portions (referred to herein as a durable housing portion and a disposable housing portion, respectively) that are configured to engage and attach to each other for operation. The disposable housing portion may contain or otherwise support an infusion medium reservoir and other components that come into contact with the infusion medium and/or the patient-user during operation. The disposable housing portion may also contain or otherwise support a pump device in accordance with one of the embodiments described herein. The pump device is connected or connectable in fluid flow communication with the reservoir, to draw fluid from the reservoir and/or convey the fluid to an injection site.

The disposable housing portion may be disengaged and separated from the durable housing portion, such that the disposable housing portion may be readily disposed of after it has been in use for a period of time, or after one or a prescribed number of uses. After disengagement and separation from a disposable housing portion, the durable housing portion may be engaged and operatively connected to another disposable housing portion (such as a new, refurbished, user-filled, pre-filled, refilled or re-manufactured disposable housing portion) for further operation. The durable housing portion may contain or otherwise support components that do not come into contact with the infusion medium or the patient-user during normal operation of the delivery device, including, but not limited to, a drive device, drive linkage, electronic circuits and, in some embodiments, a power source.

Delivery device embodiments described herein may employ any one of various pump embodiments described herein, to draw the infusion medium from the reservoir and/or convey the infusion medium to an injection site. Particular pump embodiments may be configured to provide a pump configuration that is operable in the manner described herein, yet is capable of being manufactured with sufficient economical economy to be included in a disposable housing portion.

While embodiments of the present invention are described herein with reference to an insulin delivery example for treating diabetes, other embodiments of the invention may be employed for delivering other infusion media to a patient-user for other purposes. For example, further embodiments of the invention may be employed for delivering other types of drugs to treat diseases or medical conditions other than diabetes, including, but not limited to drugs for treating pain or certain types of cancers, pulmonary disorders or HIV. Further embodiments may be employed for delivering media other than drugs, including, but not limited to, nutritional media including nutritional supplements, dyes or other tracing media, saline or other hydration media, or the like. Also, while embodiments of the present invention are described herein for delivering or infusing an infusion medium to a patient-user, other embodiments may be configured to draw a medium from a patient-user.

Furthermore, while embodiments of the present invention refer to the housing portions of disclosed delivery devices as disposable or durable, and may be configured to allow the disposable housing portion to be disposed of and replaced in an economically efficient manner, it will be understood that, in further embodiments, the disposable housing portion embodiments described herein may be re-used and need not be disposed of. Similarly, the durable housing portion embodiments described herein may be disposed of after one or more uses, if desired. However, embodiments are configured to allow certain components (for example, those that contact the infusion medium or the patient-user during operation) to be housed in a first housing portion that may be readily disposable, while other components (for example, those that do not contact the infusion medium or the patient-user during operation and that have a replacement cost that is of a relatively significant level) may be housed in a second housing portion that may be re-used with one or more new, user-filled, pre-filled, refilled, refurbished or remanufactured disposable first housing portions.

A generalized representation of an infusion medium delivery system 10 is shown in FIG. 1, wherein the system includes a delivery device 12 configured according to an embodiment of the invention described herein. The system 10 may also include other components coupled for communication with the delivery device 12, including, but not limited to, a sensor or monitor 14, a command control device (CCD) 16 and a computer 18. Each of the CCD 16, the sensor or monitor 14, the computer 18 and the delivery device 12 may include receiver, transmitter or transceiver electronics that allow communication with other components of the system. The delivery device 12 may include electronics and software for analyzing sensor data and for delivering the infusion medium according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the system 10 may include a delivery device 12 that operates without any one or more of the other components of the system 10 shown in FIG. 1. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," U.S. patent application Ser. No. 09/813,660 filed Mar. 21, 2001, and entitled "Control Tabs For Infusion Devices And Methods Of Using The Same," all of which are incorporated herein by reference in their entirety.

In the generalized system diagram of FIG. 1, the delivery device 12 and sensor or monitor 14 are secured to a patient-user 1. The locations at which those components are secured to the patient-user 1 in FIG. 1 are provided only as a representative, non-limiting example. The delivery device 12 and sensor or monitor 14 may be secured at other locations on the patient-user 1, and such locations may depend upon the type of treatment to be administered by the system 10. Such other locations may include, but are not limited to, other locations on the patient-user's body, locations on the patient-user's clothing, belt, suspenders, straps, purse, tote or other structure that may be carried by the patient-user.

As described in further detail below, the delivery device 12 contains a reservoir of an infusion medium and a pump, for delivering the infusion medium, such as, but not limited to an insulin formulation, into the patient-user's body in a controlled manner. Control instructions and/or data may be communicated between the delivery device 12, the sensor or monitor 14, the CCD 16 and the computer 18. The delivery device 12 may be configured to secure to the skin of a patient-user 1, in the manner of a patch, at a desired location on the patient-user. In such embodiments, it is desirable that the delivery device 12 have relatively small dimensions for comfort and ability to conceal the device, for example, under a garment.

Figure 2:
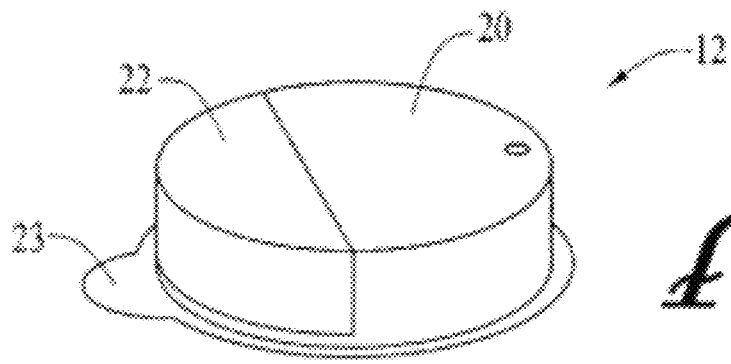
FIG. 2 is a perspective view of a delivery device according to an embodiment of the invention.
Figure 3:
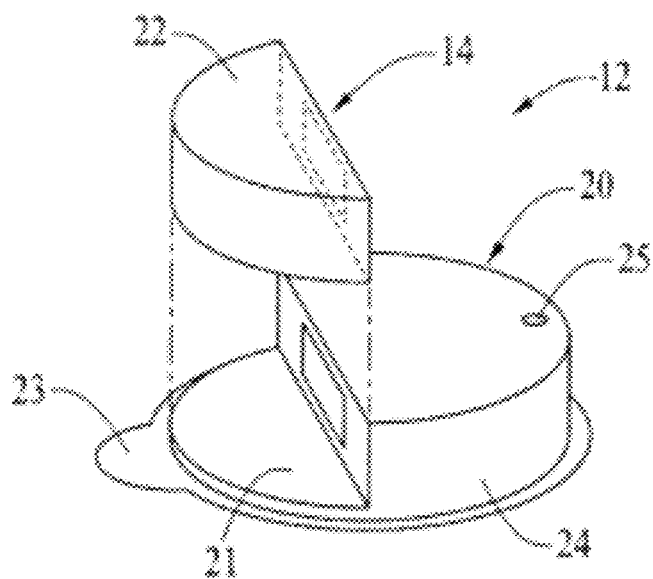
FIG. 3 is a perspective view of a durable portion and a disposable portion of the delivery device of FIG. 2, with the durable portion separated from the disposable portion.

Examples of patch-like delivery devices are described in U.S. patent application Ser. No. 11/211,095, filed Aug. 23, 2005, which is incorporated herein, in its entirety. Delivery devices described in U.S. patent application Ser. No. 11/211,095 employ a reservoir structure having a moveable plunger for selectively driving fluid from the reservoir. An example of a patch-like delivery device 12 is shown in FIGS. 2-3 herein which, according to one embodiment of the present invention, may employ a pump and drive arrangement such as shown and described with respect to FIGS. 4-7 or FIGS. 8 and 9. Further delivery device embodiments may employ a pump and drive arrangement such as shown and described with respect to FIGS. 10-15. Yet further delivery device embodiments may employ a pump and drive arrangement such as shown and described with respect to FIGS. 16 and 17. Yet further delivery device embodiments may employ a pump and drive arrangement such as shown and described with respect to FIGS. 18-20. The delivery device 12 in FIG. 2 includes a base housing portion 20 that, in some embodiments, may be disposable after one or a number of specified uses, and a further housing portion 22. For convenience, but without limitation, the base portion 20 is referred to herein as a disposable housing portion or disposable portion, while the further housing portion 22 is referred to herein as a durable housing portion or durable portion. However, as noted above, in operation, either or both housing portions 20 or 22 may be disposed of or re-used, depending upon the context of use.

The disposable housing portion 20 may support structural elements that ordinarily contact the patient-user's skin or the infusion medium, during operation of the delivery device 12. On the other hand, the durable housing portion 22 may support elements (including electronics, motor components, linkage components, and the like) that do not ordinarily contact the patient-user or the infusion medium during operation of the delivery device 12. Thus, elements in the durable housing portion 22 of the delivery device 12 are typically not contaminated from contact with the patient-user or the infusion medium during normal operation of the delivery device 12.

In the illustrated embodiment, the disposable housing portion 20 of the delivery device 12 includes a base 21 that includes or otherwise supports a reservoir retaining portion 24 that houses a reservoir and a pump device. The durable housing portion 22 may include a housing that secures onto the base 21 adjacent the reservoir retaining portion 24. The durable housing portion 22 may house a suitable drive device, such as an electrically operated motor (not shown in FIG. 2), and drive linkage components (not shown in FIG. 2) for operatively coupling the drive device to the pump to drive fluid out of the reservoir, when the durable housing portion 22 is coupled to the disposable housing portion 20. The durable housing portion 22 also may house suitable control electronics (not shown in FIG. 2) for controlling the operation of the drive device to drive fluid from the reservoir in a controlled manner. Further embodiments may include other electronics within the durable housing portion 22, such as, but not limited to communication electronics (not shown in FIG. 2) for communicating with the sensor or monitor 14, the CCD 16, the computer 18 and/or other components of the system 10 shown in FIG. 1.

The base 21 of the disposable housing portion 20 has a bottom surface (facing downward and into the page in FIGS. 2 and 3) that is configured to secure to a patient-user's skin at a desired location on the patient-user. A suitable adhesive may be employed at the interface between the bottom surface of the base 21 and the patient-user's skin, to adhere the base 21 to the patient-user's skin. The adhesive may be provided on the bottom surface of the base 21, with a peelable cover layer 23 covering the adhesive material. In this manner, a patient-user may peel off the cover layer 23 to expose the adhesive material and then place the adhesive side of the base 21 against the patient-user's skin. In further embodiments described below, multiple layers of adhesive material, alternating with multiple layers of cover layer material may be provided on the base 21, to allow the base to be secured to, removed from and then, again, secured to a patient-user's skin for multiple re-uses or re-applications. As described in further detail below, multiple alternating layers of adhesive material and peelable covers may be employed, for multiple applications or re-applications of the base 21 to the patient-user's skin.

The disposable portion 20 may include a button or other operator 25 for operating a needle insertion mechanism located within the reservoir retaining portion 24. Alternatively, or in addition, reference number 25 may represent an opening, through which an external needle insertion mechanism may operate. Examples of suitable needle insertion mechanisms are described in U.S. patent application Ser. No. 11/211,095, filed Aug. 23, 2005, and U.S. Provisional Patent Application No. 60/839,840, filed Aug. 23, 2006, titled "Infusion Medium Delivery Device, System And Method With Needle Inserter And Needle Inserter Device And Method", each of which is incorporated herein by reference in its entirety. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety. Alternatively, the reservoir retaining portion may include a suitable opening or port for connecting one end of a hollow tube to the reservoir, while the other end of the hollow tube is connected to a hollow needle for piercing the patient-user's skin and conveying the infusion medium from the reservoir into the patient-user, for example, as described with reference to FIG. 2 of U.S. patent application Ser. No. 11/211,095, filed Aug. 23, 2005.

The durable housing portion 22 of the delivery device 12 includes a housing shell configured to mate with and secure to the disposable housing portion 20. The durable housing portion 22 and disposable housing portion 20 may be provided with correspondingly shaped grooves, notches, tabs or other suitable features that allow the two parts to easily connect and disconnect from each other (for example, by a friction connection, snap connection, flexible or moveable interlocking members or other suitable connection arrangement), by manually pressing the two portions together in a manner well known in the mechanical arts. In a similar manner, the durable housing portion 22 and disposable portion 20 may be separated from each other by manually applying sufficient force to unsnap the two parts from each other. In further embodiments, a suitable seal, such as an annular seal, may be placed along the peripheral edge of the disposable housing portion 20 and/or the durable housing portion 22, so as to provide a liquid, hermetic, or air-tight seal between the durable portion 20 and the durable portion 22.

The durable housing portion 22 and disposable housing portion 20 may be made of suitably rigid materials that maintain their shape, yet provide sufficient flexibility and resilience to effectively snap together and apart, as described above. The base 21 material may be selected for suitable compatibility with the patient-user's skin. For example, the disposable housing portion 20 and the durable housing portion 22 of the delivery device 12 may be made of any suitable plastic, metal, composite material or the like. The disposable housing portion 20 may be made of the same type of material or a different material relative to the durable housing portion 22. The disposable and durable housing portions may be manufactured by injection molding or other molding processes, machining processes or combinations thereof.

The base 21 may be made of a relatively flexible material, such as a flexible silicone, plastic, rubber, synthetic rubber or the like. By forming the base 21 of a material capable of flexing with the patient-user's skin, a greater level of patient-user comfort may be achieved when the base is secured to the patient-user's skin. Also, a flexible base 21 can result in an increase in the site options on the patient-user's body at which the base 21 may be secured.

The disposable housing portion 20 and/or the durable housing portion 22 may include an internal sensor (not shown in FIGS. 2 and 3) for connection to a patient-user, for example, through a needle (not shown in FIGS. 2 and 3) for piercing a patient-user's skin when the disposable housing portion 20 is secured to a patient-user's skin. In such embodiments, a suitable aperture (not shown in FIGS. 2 and 3) may be formed in the base 21, to allow the passage of the sensor needle, when the sensor needle is extended to pierce a patient-user's skin. Alternatively, the durable housing portion 20 of the delivery device 12 may be connected to an external sensor 14, through a sensor lead, as described with respect to FIG. 2 of U.S. patent application Ser. No. 11/211,095, filed Aug. 23, 2005, titled "Infusion Device And Method With Disposable Portion." The sensor may include any suitable biological sensing device, depending upon the nature of the treatment to be administered by the delivery device 12. For example, in the context of delivering insulin to a diabetes patient, the sensor 14 may include a blood glucose sensor. Alternatively, or in addition, one or more environmental sensing devices may be included in or on the delivery device 12, for sensing one or more environmental conditions. In further alternatives, the sensor may be included with as a part or along side the infusion cannula and/or needle, such as for example as shown in U.S. patent Ser. No. 11/149,119 filed Jun. 8, 2005, and entitled "Dual Insertion Set," which is incorporated herein by reference in its entirety.

As described above, by separating disposable elements of the delivery device 12 from durable elements, the disposable elements may be arranged on the disposable portion 20, while durable elements may be arranged within a separable durable portion 22. In this regard, after one (or a prescribed number) of uses of the delivery device 12, the disposable portion 20 may be separated from the durable portion 22, so that the disposable portion 20 may be disposed of in a proper manner. The durable portion 22 may, then, be mated with a new (un-used, user-filled, pre-filled, refilled, refurbished or re-manufactured) disposable portion 20 for further delivery operation with a patient-user. This also provides the user with the option to change medication delivery, by changing out and replacing reservoirs 26 with different ones containing either different medications, such as Amilyn, GLP-1, Byetta, Peptide C, insulin sensitizers, combinations of medications (with or without insulin) or the like. Alternatively, the user my change out different types of insulin (e.g., long acting, fast acting, or the like) or utilize different concentrations (U50, U100, U200, U400 or the like).

An example of a disposable housing portion 20 and a durable housing portion 22 of a delivery device 12 according to an embodiment of the invention is shown in FIGS. 4-7, wherein FIGS. 4 and 5 show a top and side view, respectively, of a disposable housing portion 20, while FIGS. 6 and 7 show a top and side cross-sectional view of a durable housing portion 22. With reference to FIG. 4, the disposable housing portion 20 includes a base portion 21 and a reservoir retaining portion 24, as described above. With reference to FIGS. 4-7, the durable housing portion 22 is configured to be manually positioned on the base portion 21, adjacent the reservoir retaining portion 24 of the disposable housing portion 20 and to be engaged with and connected to the disposable housing portion 20, yet be selectively separable from the disposable housing portion 20, by manual force. When the durable housing portion 22 is engaged and connected with the disposable housing portion 20, a drive device within the durable housing portion 22 is arranged to make an operative connection with a pump device located within the disposable housing portion 20, as described below.

A reservoir 26 is located in the reservoir retaining portion 24. The reservoir 26 may include a container having an internal volume for containing a fluidic infusion medium, such as, but not limited to an insulin formulation. The reservoir 26 may be made of any material suitably compatible with the infusion medium, including, but not limited to suitable metal, plastic, ceramic, glass, composite material or the like. For example, the reservoir 26 may be formed of a plastic material referred to as TOPAS (trademark of Ticona, a subsidiary of Celanese Corporation), such as described in U.S. patent application Ser. No. 11/100,188, filed Apr. 5, 2005 (Publication No. 2005/0197626), the entire contents of which are incorporated herein by reference.

The reservoir 26 may be supported by the reservoir retaining portion 24 of the disposable housing portion 20 in any suitable manner. For example, the reservoir 26 may be supported on a surface of the base 21 and held in place by one or more projections, walls or other surfaces. In some embodiments, the reservoir 26 may be configured to be removable and replaceable with respect to the disposable housing portion 20. In other embodiments, the reservoir 26 may be secured to the disposable housing portion 20 in a manner intended to inhibit removal of the reservoir 26 from the disposable housing portion 20. For example, an adhesive material may be employed to adhere a surface of the reservoir 26 to the base 21 or other structure of the disposable housing portion 20. In further embodiments, multiple layers of adhesive material, alternating with multiple layers of cover layer material may be provided on the reservoir 26 or the base 21, to allow the reservoir to be secured to, removed from and then, again, secured to the base or replaced with another reservoir to secure to the base, for reservoir replacement, refilling, or other service.

In yet other embodiments, the reservoir 26 may be formed unitarily with the reservoir retaining portion 24, for example, as a hollow chamber provided within an otherwise solid portion of the reservoir retaining portion 24. In such embodiments, the hollow interior of the reservoir retaining portion 24 may be coated or lined in another manner with a suitable metal, plastic, plastic TOPAS (trademark of Ticona, a subsidiary of Celanese Corporation), ceramic, glass, composite material or the like. Alternatively, or in addition, the retaining portion 24, itself, may be made of a suitable metal, plastic, plastic, TOPAS (trademark of Ticona, a subsidiary of Celanese Corporation), ceramic, glass, composite material or the like.

The reservoir 26 has an outlet port 30, through which the infusion medium contained within the interior of the reservoir 26 may be communicated out of the reservoir. The outlet port 30 is open to the interior of the reservoir 26 and may include suitable tube-connection structure for connecting a fluid conduit 32 in fluid flow communication with the outlet port. The connection structure may include any suitable connection structure that may be selectively (or, in some embodiments, permanently) connected to a reservoir 26 to provide fluid flow communication with the interior of the reservoir 26. For example, the connection structure may function with a pierceable septum located within the outlet port of the reservoir. In such embodiments, the connection structure may include a typical Luer-type connector having a cap structure for receiving an outlet port of the reservoir and a hollow needle for piercing the septum in the outlet port of the reservoir 26 (such as, but not limited to, the reservoir connector 86 described in U.S. Patent Application Ser. No. 60/839,840, filed Aug. 23, 2006, titled "Infusion Medium Delivery Device, System And Method With Needle Inserter And Needle Inserter Device And Method", which is incorporated herein by reference, in its entirety. Further examples of needle/septum connectors can be found in U.S. patent application Ser. No. 10/328,393 filed Dec. 22, 2003, and entitled "Reservoir Connector," which is incorporated herein by reference in its entirety. In other alternatives, non-septum connectors such as Luer locks, or the like may be used. The conduit 32 may include any suitable structure that provides a fluid flow path, such as, but not limited to a tube-shaped conduit made of any suitable material, including, but not limited to silicone or other plastic, metal, ceramic or composite material.

A first end of the conduit 32 is connected or connectable to the reservoir, through a reservoir connection structure as described above. A second end of the conduit 32 is connected in fluid flow communication with an inlet port 33 of a pump device 34. The pump device 34 has an outlet port 35 connected in fluid flow communication with a second conduit 36, for conveying fluid to a delivery or injection site 38 located on the disposable housing portion 20. The injection site 38 may include an insertion mechanism to assist the insertion of a needle or cannula into the patient-user and connection of the needle or cannula in flow communication with the second conduit 36. Examples of such insertion mechanisms that are built into a delivery device are described in U.S. patent application Ser. No. 11/211,095, filed Aug. 23, 2005, titled "Infusion Device And Method With Disposable Portion" and U.S. Patent Application Ser. No. 60/839,840, filed Aug. 23, 2006, titled "Infusion Medium Delivery Device, System And Method With Needle Inserter And Needle Inserter Device And Method" (each assigned to the assignee of the present invention), each of which is incorporated herein by reference in its entirety. Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

A first valve 40 may be provided within the first conduit 32 (or between the first conduit 32 and the reservoir 26 or the inlet port 33 of the pump device 34) for restricting fluid flow to one direction from the reservoir 26 to the inlet port 33 of the pump device 34. A second valve 42 may be provided within the second conduit 36 (or between the second conduit 36 and the injection site 38 or the outlet port 35 of the pump device 34) for restricting fluid flow to one direction from the outlet port 35 of the pump device 34 to the injection site 38. Any suitable one-way valve structure may be employed for valves 40 and 42.

The example embodiment of a pump device 34 in FIG. 4 includes a pump chamber 44 having an internal volume 45 and moveable piston having a piston head 46 located within the pump chamber 44 and a piston shaft 50 extending from the piston head. The piston head 46 is selectively moveable from a retracted position (as shown in FIG. 4) in the direction of arrow 48, to an active position, to reduce the volume of the portion of the chamber 44 on the outlet port side of the piston head 46. The piston head 46 is also moveable from the active position toward the direction opposite of the arrow 48, to the retracted position (as shown in FIG. 4), to increase the volume of the portion of the chamber 44 on the outlet port side of the piston head 46.

The piston head 46 is fixedly connected to the piston shaft 50. The piston shaft 50 defines a longitudinal axis A that extends along the linear direction of movement of piston 46 (the linear direction of and opposite of the arrow 48) and has a first end that is connected to the piston head. The piston head 46 and the piston shaft 50 may include a unitary body. Alternatively, the piston head 46 and the piston shaft 50 may include two members that are coupled together in a fixed relation to each other. The second end of the piston shaft 50 is fixedly connected to a push plate 52. The push plate 52 and the piston shaft 50 may include a unitary body. Alternatively, the push plate 52 and the piston shaft 50 may include two members that are coupled together in a fixed relation to each other. The piston head 46, piston shaft 50 and push plate 52 may be made of any suitably rigid material or materials, including, but not limited to metal, plastic, ceramic, composite material or the like.

The push plate 52 may be located within a second chamber 54 that is spaced from the piston chamber 44, but connected to the piston chamber 44 by a channel section 56. The channel section 56 may include a hollow, tubular structure having an internal passage through which the piston shaft 50 extends. One or more seals 58 may be located within or adjacent to the internal passage of the channel section 56, such as, but not limited to one or more o-ring seals or the like, for inhibiting fluid from passing through the channel section 56. The seal(s) 58 may be made of any suitable seal material, including, but not limited to, plastic, rubber, silicone, metal, ceramic or composite material.

A bias member 60 is operatively connected to the piston, for example, by operative connection with the push plate 52, to provide a bias force on the piston for urging the piston along the linear dimension of the axis A, opposite to the direction of arrow 48. In the embodiment of FIG. 4, the bias member 60 includes a coil spring arranged within the second chamber 54, around and coaxial with the longitudinal axis A of the piston shaft 50. The coil spring bias member 60 of FIG. 4 has one end that abuts an internal wall of the second chamber 54 and a second end that abuts a first surface of the push plate 52. The coil spring bias member 60 is configured to be in a partially compressed state, to impart a force on the push plate 52 in the direction opposite to the direction of arrow 48. The first surface of the push plate 52 may include an annular groove in which one end of the coil spring bias member 60 may reside, to help retain the coil spring bias member 60 in place. A similar annular groove may be provided in the surface of the interior wall of the second chamber 54 that is abutted by the coil spring bias member, in which the other end of the coil spring bias member may reside.

In one embodiment, each of the pump chamber 44 and the second chamber 54 include a generally cylindrical body, having a hollow interior. In such an embodiment, the channel section 56 may include a generally hollow, cylindrical section extending between the pump chamber 44 and the second chamber 54 and having a generally cylindrical interior volume. Also in such embodiments, each of the piston head 46 and the push plate 52 may include disk-shaped members and the piston shaft 50 may include a cylindrical member, each having a generally circular cross-section (taken perpendicular to the axis A). However, in other embodiments, such structural elements having other suitable shapes may be employed. The pump chamber 44, second chamber 54 and channel section 56 may include a single, unitary structure. In alternative embodiments, the pump chamber 44, second chamber 54 and channel section 56 may be composed of one or more separate parts that are connected together in a fixed relation to each other. The pump chamber 44, second chamber 54 and channel section 56 may be made of any suitably rigid material or materials, including, but not limited to metal, plastic, ceramic, composite material or the like. In one embodiment, the second chamber 54 may be configured unitarily with the housing structure that forms the reservoir retaining portion 24 of the disposable housing portion 20. The housing structure of the reservoir retaining portion 24 may define an interior volume (for containing the reservoir 26, conduits 32 and 36, components of the injection site 38 and components of the pump device 34) that is sealed from the external environment by the walls of the housing structure, the seal 58 and a septum or other seal structure in the delivery site 38, prior to operation of a needle injector at the injection site.

The reservoir retaining portion 24 of the disposable housing portion 20 has a side or wall 66 that has an opening (which may be a recess) 68 through which the push plate 52 may be acted upon. For example, a second surface of the push plate 52 (facing in an opposite direction relative to the facing direction of the first surface against which the coil spring bias member 60 abuts) may be exposed through the opening 68 and faces in a direction outward from the opening 68. The push plate is arranged to be engaged by (or otherwise acted upon) a portion of a drive linkage supported on the durable housing portion 22, upon the durable housing portion 22 and disposable housing portion 20 being engaged and connected together for operation, as described below.

The durable housing portion 22 has a side or wall 70 (FIG. 6) that faces the wall 66 of the reservoir retaining portion 24 of the disposable housing portion 20, when the durable housing portion 22 is engaged with the disposable housing portion 20 as shown in FIG. 2. The side or wall 70 defines an opening 72 through which a portion of a linkage structure may extend, to contact and act upon the push plate 52, when the durable housing portion 22 is engaged with the disposable housing portion 20.

As described above, the durable housing portion 22 is configured to engage and connect to the disposable housing portion 20, yet be disconnected and separated from the disposable housing portion 20 by application of sufficient manual force. Any suitable connection structure, including, but not limited to, engagable snap fitted members, friction fitted members, flexible or moveable interlocking members or the like may be employed on the disposable housing portion and durable housing portion. In the embodiment shown in FIGS. 4-6, the connection structure includes a pair of engagement pawls 74 extending from the wall 66 of the reservoir retaining portion 24 of the disposable housing portion 20 and a pair of correspondingly shaped receptacles 76 on the wall 70 of the durable housing portion 22. Each engagement pawl 74 is configured to fit within an associated one of the receptacles 76, when the durable housing portion 22 is aligned with the disposable housing portion 20 in an engagement position, to connect the durable housing portion 22 and the disposable housing portion 20 together.

Each engagement pawl 74 may include a structure extending from the wall 66 and having a stop surface 78 for engaging a corresponding stop surface 79 of a receptacle 76, when the engagement pawl 74 is inserted into its associated receptacle 76. The stop surfaces 78 and 79, when engaged, inhibit separation of the durable housing portion 22 and the disposable housing portion 20, unless a sufficient separation force is applied. Preferably, the relative flexibility and resiliency of the pawls 74 and/or receptacles 76 allow the durable housing portion 22 and the disposable housing portion 20 to remain connected to each other unless a sufficient manual force is applied in the separation directions (for example the disposable housing portion is forced in a direction of arrow 48 relative to the durable housing portion and/or the durable housing portion is forced in a direction opposite to arrow 48 relative to the disposable housing portion). A sufficient force would cause the pawls 74 and/or receptacles 76 to resiliently flex enough to allow the stop surface 78 of each pawl 74 to ride over the stop surface 79 of its associated receptacle and, thus, allow the pawls 74 to be withdrawn from the receptacles 76, as the disposable portion 20 is separated from the durable portion 22.

Each pawl 74 may include an angled or curved surface (surface at an angle or having a tangent that is not parallel or perpendicular to external surface of the wall 66) to facilitate insertion of the pawls 74 into the receptacles 76. The pawls 74 may be made of a material having sufficient rigidity and flexibility to function as described herein, including, but not limited to, metal, plastic, composite material or the like. The pawls 74 may be made of the same material as and may be formed unitary with the wall 66 of the disposable housing portion 22. In other embodiments, the pawls 74 may be formed separately from the disposable housing portion and then connected to the wall 66. While the illustrated embodiment shows a pair of pawls 74 and a corresponding pair of receptacles 76, other embodiments may employ a single pawl and associated receptacle or more than two pawls and associated receptacles. Also, while the illustrated embodiment shows pawls 74 on the wall 66 of the disposable housing portion 20 and receptacles 76 on the wall 70 of the durable housing portion 22, other embodiments may employ one more pawls on the wall 70 of the durable housing portion 22 and one or more associated receptacles on the wall 66 of the disposable housing portion 20. Yet other embodiments may employ various combinations of one or more pawls and associated receptacles on each of the walls 66 and 70.

The durable housing portion 22 includes a housing structure having an interior volume 80. A drive device 82 is supported in interior volume of the durable housing portion 22 and is operatively connected to a drive shaft 84, through a linkage structure 86. The drive device 82 may include, for example, but is not limited to a motor or other device for converting electrical power into rotational motion. Such drive devices may include, but are not limited to, a DC motor, a flat or pancake DC motor, a servo motor, a stepper motor, an electronically commutated motor, a rotary piezo-electrically actuated motor, a piezo-electrically actuated or thermally actuated bender with or without an escapement wheel, an electronically actuated solenoid with or without an escapement wheel or a shaped memory alloy wire with or without an escapement wheel. Various examples of escapement wheel arrangements with benders, solenoids, shaped memory alloy wires or the like are described in U.S. Patent Application Ser. No. 60/839,822, filed Aug. 23, 2006, titled "Infusion Medium Delivery Device And Method For Driving Plunger In Reservoir", which is incorporated herein by reference in its entirety. Further examples of shape memory alloy wire drive systems may be found in U.S. Pat. No. 6,375,638 issued Apr. 23, 2002, and entitled "Incremental Motion Pump Mechanisms Driven by Shape Memory Alloy Wire or the Like," and U.S. patent application Ser. No. 11/230,142 filed Sep. 19, 2005, and entitled "SMA Wire Driven Positive Displacement Micro-Pump With Pulsatile Output," both of which are incorporated herein by reference in their entirety.

The linkage structure 86 may include any suitable gear, gear train, belt, shaft or other linkage arrangement that communicates rotational motion of the motor or other rotational motion producing device to linear motion of the drive shaft 84. In the embodiment of FIG. 6, the linkage structure includes a drive cam 90 that is coupled for rotation with a drive gear 92, about a rotational axis 94. The drive shaft 84 has one end coupled to the drive cam, at a location offset from the rotational axis 94, such that rotation of the drive cam results in linear motion of the drive shaft 84. The drive gear 92 is arranged to be rotationally driven about the axis 94 by the motor or other rotational drive device, for example, by direct connection to the motor or other rotational drive device or by indirect connection through other portions of the linkage structure 86, such as, but not limited to gears, shafts, belts or the like. Further examples of linkage structures may be found in U.S. patent application Ser. No. 09/813,660 filed Mar. 21, 2001, and entitled "Control Tabs For Infusion Devices And Methods Of Using The Same," which is incorporated herein by reference in its entirety.

In other embodiments, the drive device 82 may include a device that converts electrical power to linear motion, including, but not limited to piezo-electrically actuated solenoid or bender, thermally actuated solenoid or bender and electrically actuated solenoid devices. In such linear motion drive device embodiments, the linkage structure 86 may include any suitable gear, gear train, belt, shaft or other linkage arrangement that communicates linear motion of the drive device to linear motion of the drive shaft 84. In further linear motion drive device embodiments, the linear motion drive device may be directly connected to the drive shaft 84 (or the drive shaft 84 may be part of the linear motion drive device, such as the drive shaft of a solenoid).

The drive device 82 is connected to a control circuit that is supported within the durable housing portion 22 of the delivery device, for controlling the operation of the drive device according to a desired infusion delivery program or profile. A delivery program or profile may be stored within a suitable electronic storage medium (not shown) located within the durable housing portion 22 and/or may be communicated to the delivery device 12 from other sources, such as a CCD 16 or a computer 18 (as shown in FIG. 1). In such embodiments, the delivery program or profile may be employed by the control circuit to control the operation of the drive device 82 in accordance with the delivery program or profile. Alternatively or in addition, the control circuit may control the drive device 82 to deliver one or more discrete volumes of the infusion medium in response to delivery demand control signals generated within the device 12 or communicated to the device 12 from other sources, such as a CCD 16 or a computer 18 (as shown in FIG. 1).

The durable housing portion 22 may contain additional electronic circuitry (not shown) for communication with external devices such as the CCD 16 or computer 18, for storage of sensor data or other data, for processing and control functions, or for other functions. The durable housing portion 22 may have a user interface (not shown) including one or more buttons, electronic display, or the like, and associated electronic interface circuitry to allow a user to access data and/or input data or instructions to control electronic circuitry within the durable housing portion 22. Examples of the types of communications and/or control capabilities, as well as device feature sets and/or program options may be found in U.S. patent application Ser. No. 10/445,477 filed May 27, 2003, and entitled "External Infusion Device with Remote Programming, Bolus Estimator and/or Vibration Alarm Capabilities," and U.S. patent application Ser. No. 10/429,385 filed May 5, 2003, and entitled "Handheld Personal Data Assistant (PDA) with a Medical Device and Method of Using the Same," both of which are incorporated herein by reference in their entirety.

The durable housing portion 22 may contain a battery, high energy capacitor or other electronic power source for providing electrical power to the drive device 82, control circuit electronics and other electronic circuitry contained in the durable housing portion 22. The control circuit electronics, other electronic circuitry and the power source are represented in FIGS. 6 and 7 by reference number 98. In such embodiments, the battery, high energy capacitor or other electronic power source may be rechargeable through a recharge connector (not shown) provided on the durable housing portion 22. Alternatively, or in addition, the power source may be removable and replaceable with respect to the durable housing portion 22. In other embodiments, a battery, capacitor or other electronic power source (not shown) may be supported on the disposable housing portion 20 and connectable to the drive device 82, control circuit and other electronic circuitry in the durable housing portion, through electrical connectors (not shown in FIGS. 4-7) that make an electrical connection upon the durable housing portion 22 being coupled to the disposable housing portion 20, without additional manual manipulation. Such electrical connectors may include one or more pairs of conductive pads, where each pair of pads is connected to opposite poles of the power source and located on any suitable surface of the disposable housing portion 20 that engages a corresponding surface on the durable housing portion 22, when the durable housing portion 22 is engaged with the disposable housing portion 20. In such embodiments, the corresponding surface of the durable housing portion 22 includes one or more corresponding pairs of conductive pads that are electrically connected to the drive device 82, control circuit and other electronic circuitry in the durable housing portion and are arranged to engage the conductive pads on the disposable housing portion, when the durable housing portion 22 is coupled to the disposable housing portion 20.

The drive device 82, linkage structure 86, control circuit, other electronic circuitry and power source 98 described above, are located within the interior volume 80 of the durable housing portion 22. As described above, the drive shaft 84 extends through an opening in the wall 70 of the durable housing portion 22. To protect those electrical and mechanical components from certain environmental conditions (such as, but not limited to, moisture, air, biological or medical fluids), the interior volume 80 of the durable portion 22 may be suitably sealed from the external environment by the housing structure that forms the durable portion 22 and by one or more seals 99 provided around the drive shaft 84, within or adjacent the opening in the wall 70. The seal(s) 99 may include, but are not limited to, one or more o-ring seals or the like. The seal(s) 99 may be made of any suitable seal material, including, but not limited to, plastic, rubber, silicone, metal, ceramic or composite material.

Accordingly, the delivery device 12 of FIGS. 4-6 includes a disposable housing portion 20 supporting a reservoir 26, a pump device 34 and other components described above, and a durable housing portion 22 for supporting a drive device 82, a drive shaft 84, linkage structure 86, and electronics (which may also include a power source) 98. To operate the delivery device 12, the reservoir in the disposable housing portion 20 may be filled with a suitable infusion medium. The disposable housing portion 20 may be secured to a patient-user's skin (either before or after filling the reservoir), in the manner described above. A needle injector may be operated to place a hollow needle or cannula through the patient-user's skin and connect the hollow needle or cannula in fluid flow communication with the conduit 36.

The durable housing portion 22 may be manually aligned with the disposable housing portion 20, and engaged with and connected to the disposable housing portion 20 (either before or after the disposable housing portion is secured to a patient-user's skin and either before or after the needle injector is activated), in the manner described above. By engaging and connecting the durable housing portion 22 with the disposable housing portion 20, an end of the drive shaft 84 (opposite to the end connected to the drive cam 90) abuts or is positioned adjacent to the push plate 52. For example, when the durable housing portion 22 is aligned to be engaged and connected with the disposable housing portion 20, the drive shaft 84 may extend into the opening in the wall 66 of the reservoir retaining portion 24 of the disposable housing portion 20 and contact or reside adjacent the outward-facing surface of the push plate 52.

Once the disposable housing portion 20 and the durable housing portion 22 are engaged and connected together, the drive device 82 may be selectively activated, with the electrical control and power provided by the control circuit electronics and power source 98, to selectively move the drive shaft 84 in a back-and-forth motion along two generally linear directions (corresponding to the direction of arrow 48 and the direction opposite to the direction of arrow 48), as described above. For example, the drive device 82 may be controlled to selectively rotate the drive gear 92 and drive cam 90 in a first direction about the rotation axis 94. As the drive cam 90 rotates, the drive shaft is moved in one direction and then the opposite direction, along the linear dimension of the arrow 48. Alternatively, the drive shaft 82 may be driven in a linear back-and-forth motion by rotating the drive gear 92 and drive cam 90 in one direction and then the opposite direction, for example, by controlling the drive device to drive in one direction and then the opposite direction.

As the drive shaft 84 is driven in the direction of arrow 48, the extended end of the drive shaft 84 engages the push plate 52 and imparts a force on the push plate 52 in the direction of arrow 48 sufficient to move the push plate 52 in the direction of arrow 48, against the force of the coil spring bias member 60. As the push plate 52 is moved in the direction of arrow 48, the piston shaft 50 and piston head 46 are moved in the direction of arrow 48, from the retracted position (as shown in FIG. 4), to an active position. As the piston head 46 moves toward the active position, the volume of the portion of the piston chamber 44 located on one side of the piston head 46 (the side to the left of the piston head 46 in the orientation shown in FIG. 4) is reduced. As that portion of the piston chamber 44 volume reduces, the pressure within that volume increases to force fluid through the outlet port 35, conduit 36 and one-way valve 42, to the injection site 38.

The amount of motion of the drive shaft 84 in the direction of arrow 48 is selected to move the piston head from the retracted position (shown in FIG. 4). Once the piston head 46 reaches its active position, the drive shaft 84 also reaches its farthest point of motion in the direction of arrow 48. Thereafter, the drive shaft 84 is moved in the direction opposite to the direction of arrow 48 as the drive device 82 continues to impart a drive force. As the drive shaft 84 moves in the direction opposite to the direction of arrow 48, the push plate 52, piston, piston shaft 50 and piston head 46 also move in the direction opposite to the direction of arrow 48 to the retracted position (shown in FIG. 4), by the force of the coil spring bias member 60.

As the piston head 46 moves in the direction opposite of the direction of arrow 48, from its active position toward its retracted position, the volume of the portion of the piston chamber 44 located on one side of the piston head 46 (the side to the left of the piston head 46 in the orientation shown in FIG. 4) increases. As that portion of the piston chamber 44 volume increases, the pressure within that volume decreases sufficiently to draw fluid from the reservoir 26, through the conduit 32, the one-way valve 40 and the inlet port 33, and into that portion of the volume of the piston chamber 44. In this manner, the portion of the volume of the piston chamber on one side of the piston head 46 (the side to the left of the piston head 46 in the orientation shown in FIG. 4) fills with infusion medium, for another stroke of the piston head 46 in the direction of arrow 48. Accordingly, the pump device 34 may be driven by the motion of the drive shaft 84, to effectively force infusion medium from the piston chamber 44 to the injection site 38, and by the return force of the bias member 60, to draw infusion medium from the reservoir 26, into the piston chamber 44. The drive device 82 may be controlled by the control circuit, in accordance with a pre-defined delivery profile, to selectively deliver a suitable amount of infusion medium to the patient-user, through the injection site. The delivery profile may be designed in accordance with a pre-known volume of the piston chamber 44 and the pre-known volume of infusion medium delivered through the outlet port 35 and conduit 36 to the injection site 38, for each stroke of the piston head 46 from the retracted position to the active position.

Before starting a pumping process, the piston chamber 44 may be primed, for example, by pre-filling the piston chamber 44 with infusion medium during manufacture, assembly or at another time period prior to securing the disposable portion of the delivery device to a patient-user's skin, by filling the piston chamber 44 either before or after securing to the patient-user through a filling port (not shown), or by operating the drive device to cause the piston head 36 to make one or more strokes to lower the pressure within the piston chamber sufficient to draw fluid from the reservoir through the inlet port 33 before activation of a needle injector at the injection site 38. In yet other embodiments, a priming port may be provided in the piston chamber 44, where the priming port may include a one-way air valve (not shown) that allows air to escape, but inhibits infusion fluid from escaping the piston chamber 44 and inhibits air from entering the piston chamber 44. In such embodiments, the priming port may be covered with a material that allows the passage of air, but inhibits the passage of water or other liquids. Examples of structures that permit air-flow, but that inhibit fluids can be found in U.S. patent application Ser. No. 10/328,393 filed Dec. 22, 2003, and entitled "Reservoir Connector," and U.S. patent application Ser. No. 10/699,429 filed Oct. 31, 2003, and entitled "External Infusion Device with a Vented Housing," both of which are incorporated herein by reference in their entirety.

The embodiment shown in FIGS. 4-6 employs a bias member 60 for imparting a force on the push plate 52, to return the push plate 52 to the retracted position (shown in FIG. 4). In such an embodiment, the drive shaft 84 may be arranged to engage and abut the push plate 52 to push the push plate 52 in the direction of arrow 48, while the bias member 60 urges the push plate 52 back toward the retracted position (in the direction opposite to the direction of arrow 48), when the drive shaft 84 is driven to the return position. Other embodiments may employ the return motion of the drive shaft 84 (in the direction opposite to the direction of arrow 48) to return the push plate 52 to the retracted position. Such embodiments may employ suitable connection structure for allowing the drive shaft 84 to be selectively engaged and connected to the push plate 52, when the durable housing portion 22 is engaged and connected to the disposable housing portion 20. Such connection structure may include, but not limited to, engageable snap fitted members, friction fitted members, flexible or moveable interlocking members or the like. In one embodiment, the connection structure for connecting the drive shaft 84 to the push plate 52 may include a pawl and associated receptacle arrangement (similar to the pawl 74 and receptacle 76 described above), wherein one of the pawl and receptacle is provided on the push plate and the other of the pawl and receptacle is provided on the end of the drive shaft 84.

As described above, the embodiment shown in FIGS. 4-6 may employ any one of various types of suitable drive devices including, but are not limited to, a DC motor, a flat or pancake DC motor, a servo motor, a stepper motor, an electronically commutated motor, a rotary piezo-electrically actuated motor, a piezo-electrically actuated or thermally actuated bender with or without an escapement wheel, an electronically actuated solenoid with or without an escapement wheel or a Shape Memory Alloy (SMA) wire with or without an escapement wheel. For example, the linear motion of the push plate 52 may be provided by an SMA wire, such as, but not limited to, Nitinol (Nickel-Titanium/Naval Ordinance Laboratory). A Nitinol driver may be provided in the durable housing portion 22 or the disposable housing portion 20.

Figure 8:
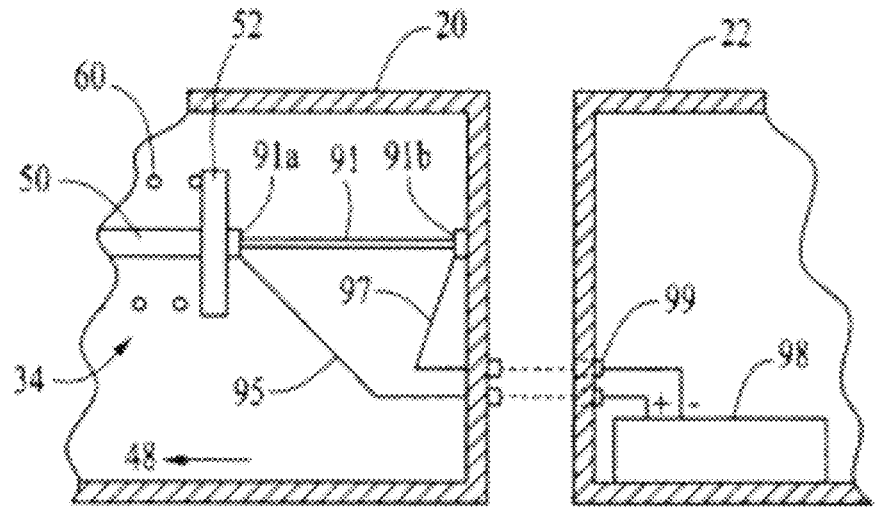
FIG. 8 shows a schematic view of a pump device and reservoir according to a further embodiment of the invention.

For example, in the embodiment of FIG. 8, an SMA wire 91 is located in the disposable housing portion 20, and has one end 91a connected to the push plate 52 (or directly to the piston shaft 50 by omitting the push plate 52) and a second end 91b connected in a fixed position relative to the disposable housing portion. The SMA wire 91 is configured to expand in the linear direction (the direction of the wire, to push the piston shaft 50 in the direction of arrow 48, upon application of a suitable electrical potential across the SMA wire. The two ends 91a and 91b of the SMA wire 91 are connected, through suitable electrical leads 95 and 97, to an electrical connector element 93 on the disposable housing portion 20.

The connector element 93 is configured to electrically connect with a corresponding connector element 93' on the durable housing portion 22, when the disposable housing portion 20 and the durable housing portion 22 are engaged. The connector element 93' is electrically connected to a battery (or other suitable source of electrical power) and control electronics 98, to selectively provide an electrical potential across the leads 95 and 97, to selectively energize the SMA wire, when the disposable housing portion 20 and the durable housing portion 22 are engaged. Because the power source in the durable housing portion 22 and the SMA wire drive device in the disposable housing portion 20 need only an electrical connection for operation, the respective housing portions 20 and 22 may be enclosed and sealed, and need not include any openings to the external environment. In further embodiments, such sealed housing portions may include a vent opening for equalizing pressure between the interior of the housing portion and the exterior environment.

In the embodiment of FIG. 8, when the durable housing portion 22 is engaged with the disposable housing portion 20, an electrical connection is made between the connector elements 93 and 93', to connect the battery and control electronics 98 to the leads 95 and 97 for the SMA wire. Application of a controlled electrical power signal to the leads 95 and 97, from the battery and control electronics 98 causes the SMA wire to expand in the linear direction. Because the end 91b of the SMA wire is connected in a fixed relation to the disposable housing portion 20, the controlled linear expansion of the SMA wire causes the second end of the SMA wire to selectively move in the direction of arrow 48, to move the push plate 52 in the direction of arrow 48. In this manner, the battery and control electronics 98 may operate the pump 34, to selectively drive fluid from the pump, to an injection site.

Figure 9:
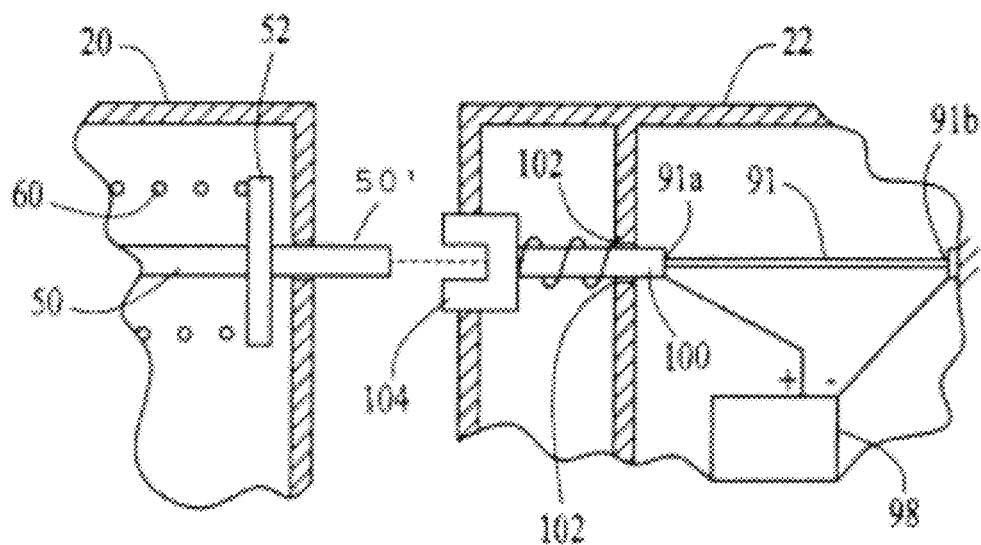
FIG. 9 shows a schematic view of a pump device and reservoir according to yet a further embodiment of the invention.

Another drive example that employs an SMA wire is shown in FIG. 9, wherein an SMA wire is located in the durable housing portion 22. In FIG. 9, the SMA wire 91' has one end 91a' coupled to a push rod 100 and a second end 91b' coupled in a fixed relation with the durable housing portion 22. The push rod 100 is supported for movement in a linear direction (the directions of arrow 48 and opposite to arrow 48), for example, by a suitable support structure 102 that includes a slide bearing surface abutting the push rod 100. The support structure 102 may be part of or affixed to the durable housing portion 22. The push rod 100 is connected to a mating member 104 that has a mating surface accessible from outside of the durable housing portion 22. A bias member provides a return force on the mating member 104 and may comprise a coil spring connected between the mating member 104 and the support structure 102.

The mating member 104 may be located external to the durable housing portion 22 and/or may extend through an opening in the durable housing portion 22, such that the mating surface of the mating member 104 is arranged to engage a corresponding mating surface on the pump device 34, when the durable housing portion 22 and the disposable housing portion 20 are engaged. In the embodiment of FIG. 9, a connection shaft 50' extends from the pump device 34 and has a mating surface on one end that is shaped to engage and mate with the mating surface of the mating member 104. In the embodiment in FIG. 9, the connection shaft 50' extends from the push plate 52. In other embodiments, the push plate 52 may be omitted, such that the connection shaft 50' comprises a portion of the piston shaft 50.

In the embodiment of FIG. 9, when the durable housing portion 22 is engaged with the disposable housing portion 20, a mechanical connection is made between the mating member 104 and the connection shaft 50. Application of a controlled electrical power signal across the SMA wire causes the SMA wire to expand in the linear direction. Because the end 91b' of the SMA wire is connected in a fixed relation to the durable housing portion 22, the controlled linear expansion of the SMA wire causes the second end of the SMA wire to selectively move in the direction of arrow 48, to move the push rod 100 and the mating member 104 in the direction of arrow 48. In this manner, the battery and control electronics 98 may operate the pump 34, to selectively drive fluid from the pump, to an injection site.

A linear-motion pump device 134 according to a further embodiment of the invention is shown in FIGS. 10-15. The pump device 134 may be employed in a delivery device 12 as described above with respect to FIGS. 4-7, in place of the linear motion pump device 34 described above. The pump device 134 includes a shuttle mechanism that is operated by imparting a linear force for providing a linear motion of a piston shuttle.

Figure 10:
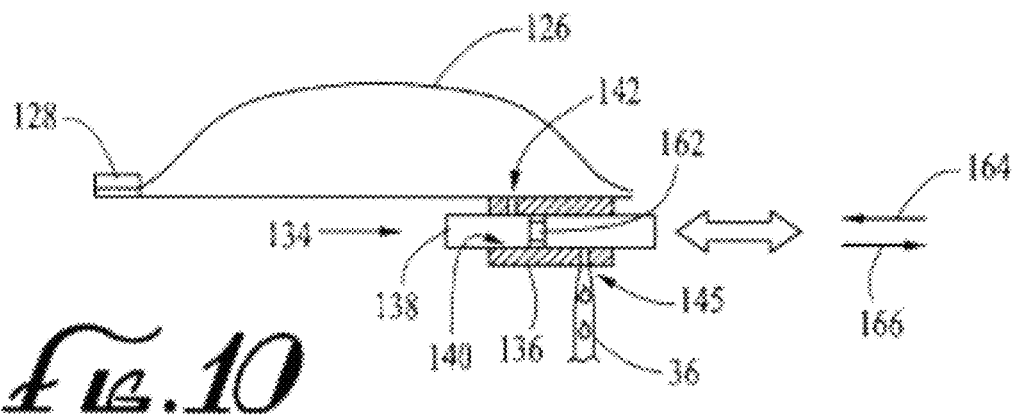
FIG. 10 shows a schematic view of a pump device and reservoir according to yet a further embodiment of the invention.

With reference to FIG. 10, the pump device 134 operates to dispense fluid from a reservoir 126. The reservoir 126 may be located in a disposable housing portion, similar to the disposable housing portion 20 described above. The reservoir 126 may include a reservoir structure as described above with respect to reservoir 26 in FIGS. 4-7. Alternatively, the reservoir 126 may include a flexible bag or a container having flexible walls that collapse, as fluid is withdrawn from the reservoir interior.

The reservoir 126 may include a septum 128, such as a self-sealing septum that may be pierced by a needle (for example a syringe needle) for filling or refilling of the reservoir. The septum 128 may be positioned at a location where it is exposed through an opening in the housing structure that forms the disposable housing portion 20, to allow access for filling or refilling operations from outside of the disposable housing portion 20. The reservoir 126 may be filled or refilled, for example, by inserting a needle of a syringe through the septum 128 and operating the syringe to dispense infusion fluid from the needle, into the interior of the reservoir.

The pump device 134 includes a shuttle housing 136 and a shuttle piston 138. The shuttle housing 136 includes a structural body made of any suitably rigid material, including, but not limited to, metal, plastic, ceramic, glass or composite materials. The shuttle housing 136 includes an interior channel 140 having a longitudinal axis $A_1$. The shuttle housing 136 may include a cylindrical-shaped body having an outer peripheral wall surface and the channel 140 may be cylindrical shaped channel generally centrally located within the cylindrical shaped body. However, other embodiments may employ other suitable shapes for the shuttle housing 136 and channel 140. The shuttle housing 136 includes an inlet port 142, comprising an opening through the outer wall of the shuttle housing 136, to the channel 140. The shuttle housing 136 also includes an outlet port 144, comprising a second opening through the outer wall of the shuttle housing 136, to the channel 140. The outlet port 144 is located at a spaced relation relative to the inlet port 142, along the longitudinal axis $A_1$ of the channel 140.

In the embodiment of FIGS. 10-15, the inlet port 142 and the outlet port 144 are offset from each other by 180 degrees around the longitudinal axis $A_1$ of the channel 140, with the inlet port 142 directed upward and the outlet port directed downward relative to the orientation of FIGS. 10-15. However, in other embodiments, the inlet port 142 and the outlet port 144 may be offset from each other by less than or greater than 180 degrees, or may be in line (not offset) with respect to the longitudinal axis $A_1$ of the channel 140. The outlet port 144 may be connected to a conduit in fluid flow communication with an injection site, such as conduit 36 and injection site 38 as shown in FIG. 4.

The piston 138 includes first and second piston sections 146 and 148, respectively. Each piston section 146, 148 includes a structural body having a longitudinal axis and a shape corresponding to the shape of the channel 140. Accordingly, in embodiments in which the channel 140 has a cylindrical shape, the structural body of the piston sections 146 and 148 each include a cylindrical shaped body having an outer diameter slightly less than the diameter of the channel 140. The diameters of the piston sections 146, 148 and the channel 140 are selected to allow the piston sections 146, 148 to fit within and move axially within the channel 140, yet inhibit leakage of infusion fluid between the piston sections 146, 148 and the interior wall of the channel 140. The piston sections 146, 148 may be made of any suitably rigid material, including, but not limited to, metal, plastic, ceramic, glass or composite materials.

Figure 11:
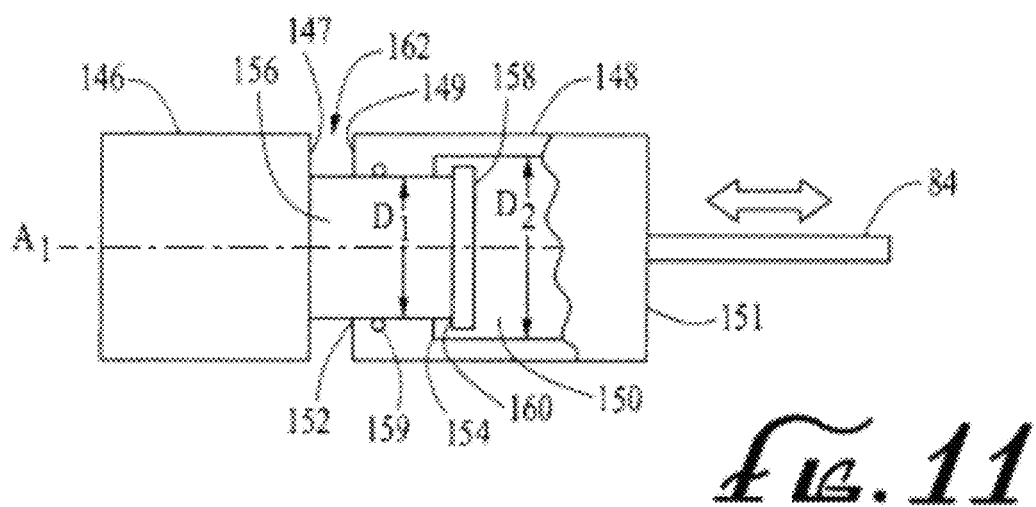
FIG. 11 shows a side, partial cross-section view of a piston of the pump device of FIG. 8, according to an embodiment of the invention.
Figure 12:
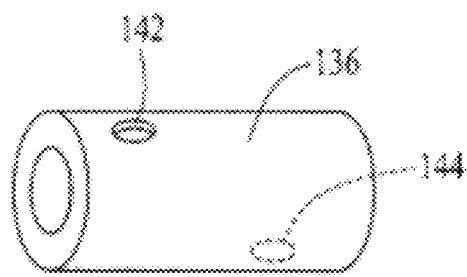
FIG. 12 shows a perspective view of a shuttle housing of the pump device of FIG. 10, according to an embodiment of the invention.

The piston sections 146, 148 are arranged, end-to-end, at least partially within the channel 140, such that one end 147 of piston section 146 faces an opposite-facing end 149 of piston section 148. The piston sections 146, 148 are separate structural bodies that are coupled together, yet moveable relative to each other in the axial dimension of the channel 140. A coupling structure suitable for allowing axial movement of the piston sections 146 and 148 relative to each other is provided to couple the piston sections 146, 148 together. One embodiment of such a suitable coupling structure is shown in FIG. 11 and includes a hollow interior channel 150 extending axially within the interior of one of the piston sections, such as the piston section 148. The end of the piston section 148 that faces the piston section 146 is provided with an opening 152 into the interior channel 150 of the piston section 148. The channel 150 of the piston section 148 has a stepped interior surface, that has a first diameter $D_1$ adjacent the opening 152 and a second diameter $D_2$ further spaced from the opening 152 along the axial dimension $A_1$. A step, forming a stop surface 154, is provided at the transition between the two diameters $D_1$ and $D_2$ of the channel 150.

The coupling structure further includes an extension portion 156, extending axially from the end of the piston section 146 that faces the piston section 148. The extension portion 156 is rigidly fixed relative to the piston section 146. The extension portion 156 may be formed integral with the piston section 146 as a single, unitary body, or may be formed separate from the piston section 146 and fixedly secured to the piston section 146. The extension portion 156 extends toward the piston section 148 and through the opening 152 in the end of the piston section 148 and into the channel 150. The extension portion 156 has a free end on which a head 158 is located. The head 158 provides a stop surface 160 for engaging the stop surface 154, as described below.

One or more seals 159, including, but not limited to o-ring seals, may be provided around the opening 152 and/or around the extension portion 156, to inhibit fluid flow communication through the opening 152 and into the channel 150. Such seal(s) 159 may be made of any suitable seal material, including, but not limited to, metal, plastic, silicone, ceramic, composite material or the like. While the coupling structure in the embodiment of FIG. 11 employs a channel 150 in the piston section 148 and an extension portion 156 on the piston section 146, other embodiments may employ a channel 150 in the piston section 146 and an extension portion on the piston section 148, to function in a manner as described herein.

The coupling structure allows the piston sections 146, 148 to move axially relative to each other to separate from each other for a limited distance, while remaining connected to each other. As one or both of the piston sections 146, 148 moves axially to separate the piston sections 146, 148, a gap or chamber 162 is formed between the two facing ends 147 and 149 of the piston sections 146 and 148, respectively. The width of the gap or chamber 162 (in the axial dimension)

increases, as one or both of the piston sections 146, 148 move to separate, until the stop surface 160 of the head 158 engages the stop surface 154 of the stepped interior surface of the channel 150. Upon engagement of the stop surfaces 160 and 154, further relative movement of the piston sections 146, 148 in a separation direction (axially away from each other) is inhibited. On the other hand, as one of the piston sections 146, 148 is moved toward the other piston section from a separated position, the gap or chamber 162 decreases in width (in the axial dimension) until the facing ends 147, 149 of the piston sections 146, 148 contact each other.

In operation, the piston 138 (including both piston sections 146, 148) is moved in a linear manner, along the axial dimension $A_1$, by selective operation of a drive device, similar to the operation of the drive device described above with respect to FIGS. 4-7. In one embodiment, the end 151 of the piston section 148 opposite to the end 149 is arranged to be acted upon by a drive shaft, such as drive shaft 84 described above with respect to FIGS. 4-7, to impart a force on the piston section 148 sufficient to provide axial motion of the piston 138 within the channel 140. For example, the shuttle housing 136 and piston 138 of the pump device 134 of FIG. 10 may be supported within the reservoir retaining portion 24 of the disposable housing portion 20 (of FIGS. 4 and 5), in place of the pump device 34 described above, and with the end 151 of the piston 138 arranged to be exposed or otherwise arranged to be acted upon through the opening 68 in the wall 66 of the disposable housing portion 20 (similar to the manner in which the end of the push plate 52 is exposed or otherwise acted upon by the drive shaft 84, through the opening 68, as described above). When the durable housing portion 22 is engaged and connected to the disposable housing portion 20, the drive shaft 84 is arranged to abut or otherwise impart a force onto the end 151 of the piston section 148.

The drive shaft 84 and the end 151 of the piston section 148 may be provided with a suitable connection structure for allowing the drive shaft 84 to be selectively engaged and connected to the end 151 of the piston section 148, when the durable housing portion 22 is engaged and connected to the disposable housing portion 20. Such connection structure may include, but is not limited to, engageable snap fitted members, friction fitted members, flexible or moveable interlocking members or the like. In one embodiment, the connection structure for connecting the drive shaft 84 to the end 151 of the piston section 148 may include a pawl and associated receptacle arrangement (similar to the pawl 74 and receptacle 76 described above), wherein one of the pawl and receptacle is provided on the push plate and the other of the pawl and receptacle is provided on the end of the drive shaft 84.

By connecting the drive shaft 84 to the end 151 of the piston section 148, the drive shaft 84 may impart forces on the piston section 148 in the direction of arrow 164 and, then in the direction of arrow 166, to provide a back-and-forth motion of the piston section 148 in the axial dimension $A_1$. The length of motion of the drive shaft 84 and the dimensions of the piston sections 146, 148 and the extensions portion 156 are selected to allow the piston sections to move (with the motion of the drive shaft 84), as described with reference to FIGS. 13-15.

Figure 14:
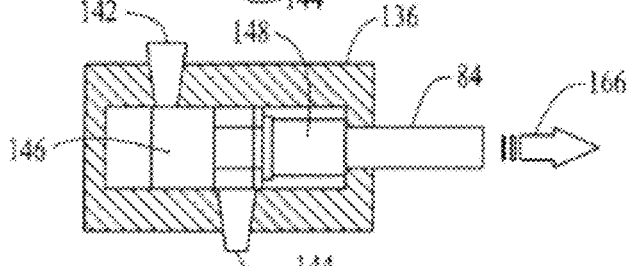
Figure 15A:
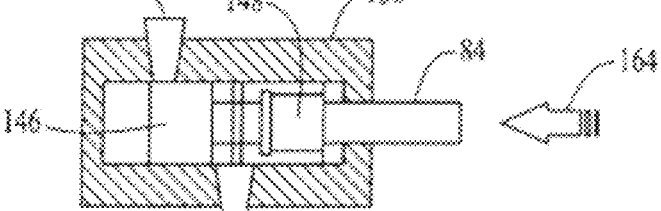
Figure 15B:
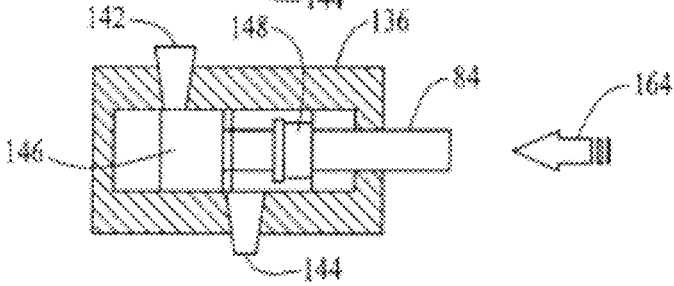

The piston 138 (including piston sections 146, 148 shown in FIGS. 13-15) are moveable along the axial dimension $A_1$, between at least three general positional locations along the axial dimension $A_1$. The three general positional locations are referred to herein as the fill position (FIGS. 13a-c), the shuttle position (FIG. 14) and the dispense position (FIGS. 15a-b).

The piston 138 may be placed in a start portion of the fill position (FIG. 13a) prior to the beginning of operation (for example, during manufacture, assembly or installation). Alternatively, the piston 138 may be in another initial position (for example the position shown in FIG. 14) prior to operation, and the drive device 82 may be initially operated to move the drive shaft 84 and, thus the piston 138 from that initial position, in the direction of arrow 164, to a start portion of the fill position (as shown in FIG. 13a).

The drive force on the piston 138 is applied by the drive shaft 84 onto the end 151 of the piston section 148. Accordingly, if the piston sections 146, 148 are initially separated, the drive force imparted by the drive shaft 84 on the piston end 151 in the direction of arrow 164, will first cause the piston section 148 to move toward the piston section 146 and close the gap or chamber 162, until the end surfaces 147 and 149 of the piston sections 146 and 148, respectively, come into contact.

Figure 13A:
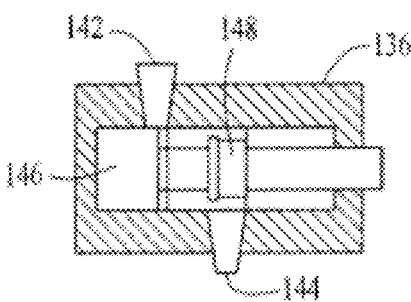
FIGS. 13a-15b show side cross-section views of the pump device of FIG. 10, in a fill, shuttle and dispense position, respectively.

In a starting (or ending) portion of the fill position, as shown in FIG. 13a, the piston 138 is arranged with the end faces 147 and 149 of the piston sections 146 and 148 adjacent the inlet port 142 and with no (or a minimal) gap between the end faces 147 and 149 of the piston sections 146 and 148. From the starting portion of the fill position of FIG. 13a, the piston section 148 may be moved in the direction of arrow 166 to open the gap or chamber 162 between the end faces 147 and 149 of the piston section.

The opening of the gap or chamber 162, while the gap or chamber 162 is sealed from the external environment, creates a low pressure volume (relative to the pressure within the reservoir 126) within the gap or chamber 162. In one embodiment, the low pressure volume within the gap or chamber 162 provides a sufficient pressure differential relative to the pressure within the reservoir 126, to cause fluid to flow into the gap or chamber 162, from the reservoir 126, through the inlet port 142. By opening the gap or chamber 162, fluid is drawn from the reservoir, through the inlet port 142 and into the gap or chamber 162. As the piston section 148 continues to move in the direction of arrow 166, the gap or chamber 162 continues to widen to the complete fill portion of the fill position, shown in FIG. 13c, at which the piston sections 146 and 148 are in a fully separated state (wherein the stop surfaces 154 and 160 of FIG. 11 are abutted together).

Figure 13B:
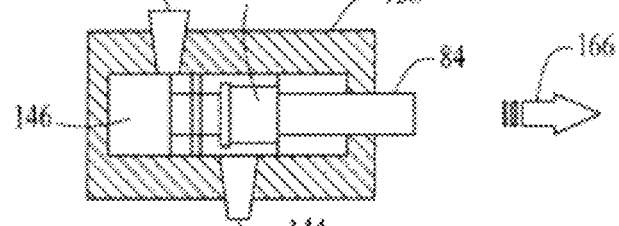
Figure 13C:
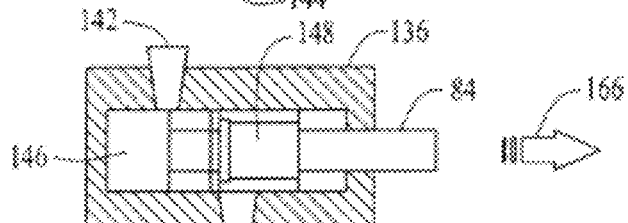

In the fill position of FIGS. 13a-c, the piston sections 146 and 148 are positioned relative to the shuttle housing 136, such that the gap or chamber 162 is located in fluid flow communication with the inlet port 142 of the shuttle housing 136. In that position, fluid flow communication is provided between the interior of the reservoir 126 and the gap or chamber 162, through the inlet port 142, to allow infusion fluid to flow from the reservoir, into the gap or chamber 162. Fluid may flow from the reservoir 126 and into the gap or chamber 162, for example, by the force of a pressure differential created when piston sections 146, 148 separate to form the gap or chamber 162 and/or by gravitational force (wherein the gap or chamber 162 is located below the reservoir 126, during operation, as shown in FIGS. 13-15). Alternatively, or in addition, fluid flow from the reservoir 126, to the gap or chamber 162 may be provided or enhanced by providing the interior of the reservoir 126 with a pressure higher than the pressure in the gap or chamber 162 (for example, by imparting a force on a flexible wall of the reservoir and/or filling the reservoir with pressurized fluid).

From the complete fill portion of the fill position of FIG. 13c, further motion of the drive shaft 84 in the direction of arrow 166 causes the piston 138 (including the piston sections 146, 148) to move in the direction of arrow 166, while the gap or chamber 162 is maintained. As the piston 138 moves in the direction of arrow 166, the gap or chamber 162 moves in the direction of arrow 166, through locations between the inlet port 142 and the outlet port 144. to a transport or shuttle position shown in FIG. 14, at which the gap or chamber 162 is aligned with the outlet port 144. The full stroke of motion of the drive shaft 84 in the direction of arrow 166 may be selected such that the end of the stroke of motion of the drive shaft 84 in the direction of arrow 166 corresponds to the position of the piston sections 146 and 148 in FIG. 14. Similarly, the full stroke of motion of the drive shaft 84 in the direction of arrow 164 may be selected such that the end of the stroke of motion of the drive shaft 84 in the direction of arrow 164 corresponds to the position of the piston sections 146 and 148 in FIG. 13a.

At the end of the full stroke of motion of the drive shaft 84 in the direction of arrow 166, the drive shaft 84 begins to move back, in the direction of arrow 164 (opposite to the direction of arrow 166). By allowing the drive shaft 84 to move a relatively small distance in the direction of arrow 164, the piston section 148 is moved in the direction of arrow 164 relative to the piston section 146 and the shuttle housing 136, as shown in FIG. 15a, to begin dispensing fluid from the gap or chamber 162, into the outlet port 144. Further motion of the drive shaft in the direction of arrow 164 causes the piston section 148 to move in the direction of arrow 166 until the end faces 147 and 149 of the piston sections 146 and 148 abut each other, as shown in FIG. 15b.

In the complete dispense portion of the dispense position (FIG. 15b), the pressure in the gap or chamber 162 is increased by driving the piston sections 146 and 148 further together, to force the infusion medium out of the gap or chamber 162 and into the conduit 36. For example, once the piston 138 has reached position at which the gap or chamber 162 is aligned with and in fluid-flow communication with the outlet port 144, (FIG. 14) the drive shaft 84 may impart a force on the end surface 151 of the piston portion 148, in the direction of arrow 164 (FIGS. 15a-b). That force causes the piston section 148 to move axially in the direction of arrow 164, relative to the piston section 146 and shuttle housing 136, until the end walls 147 and 149 (FIG. 11) of the piston sections 146, 148 abut each other. As the piston section 148 moves toward the piston section 146, the volume of the gap or chamber 162 decreases, causing the infusion medium within the gap or chamber to be forced out of the gap or chamber and be dispensed into the conduit 36, through the outlet port 144.

The piston section 146 may be configured to provide a bi-directional friction with the interior surface of the piston channel 140 of the cylinder 136 that is greater than that of the piston member 148 in the cylinder 136. In the fill stroke direction 166, the piston section 146 is held back relative to the motion of the piston member 148, to open the chamber 162. In the dispense stroke direction 164, the piston section 146 resists motion relative to the motion of the piston section 148 to fully force the fluid from the chamber into the outlet port 144. This bi-directional friction for the piston section 146 may be provided by selecting the shape and/or size of the outer diameter of the piston section 146, or by providing a spring-loaded or otherwise biased member to bear against the piston section 146, to provide suitable friction engagement with the inside surface of the piston channel 140 and/or by providing one or more O-ring seals around the piston section 146.

A reservoir 126, piston 138 and shuttle housing 136 configuration, as shown in FIGS. 10-15 may be employed in a disposable housing portion 20, as described above, in place of the pump device 34 and reservoir 26 described above with respect to FIGS. 4-7). The piston 138 may be operatively coupled to a drive shaft 84, as described above, when a durable housing portion 22 is coupled to the disposable housing portion 2, to control movement of the piston 138 in a back-and-forth motion along the axial dimension $A_1$ (in the directions of arrows 164 and 166).

With the configuration of FIGS. 10-15, such movement of the piston 138 causes the piston sections 146, 148 to move between the fill position (FIG. 11), the shuttle position (FIG. 12) and the dispense position (FIG. 13) and back, within the shuttle housing 136. Such motion of the piston sections 146, 148 causes a volume of infusion medium to be dispensed from the outlet port 144 and into the conduit 136, with each back-and-forth motion of the piston 138. The volume of infusion medium dispensed with each back-and-forth motion of the piston 138 is dependent on the volume of the gap or chamber 162 and may be pre-determined for providing a suitable delivery profile to control the operation of the drive device 84. Accordingly, the pump device embodiment of FIGS. 10-15 may be operatively coupled to a linearly driven drive shaft, to allow for a controlled dispensing of infusion medium, with relatively few moving parts and relatively uncomplicated structural components.

Figure 17:
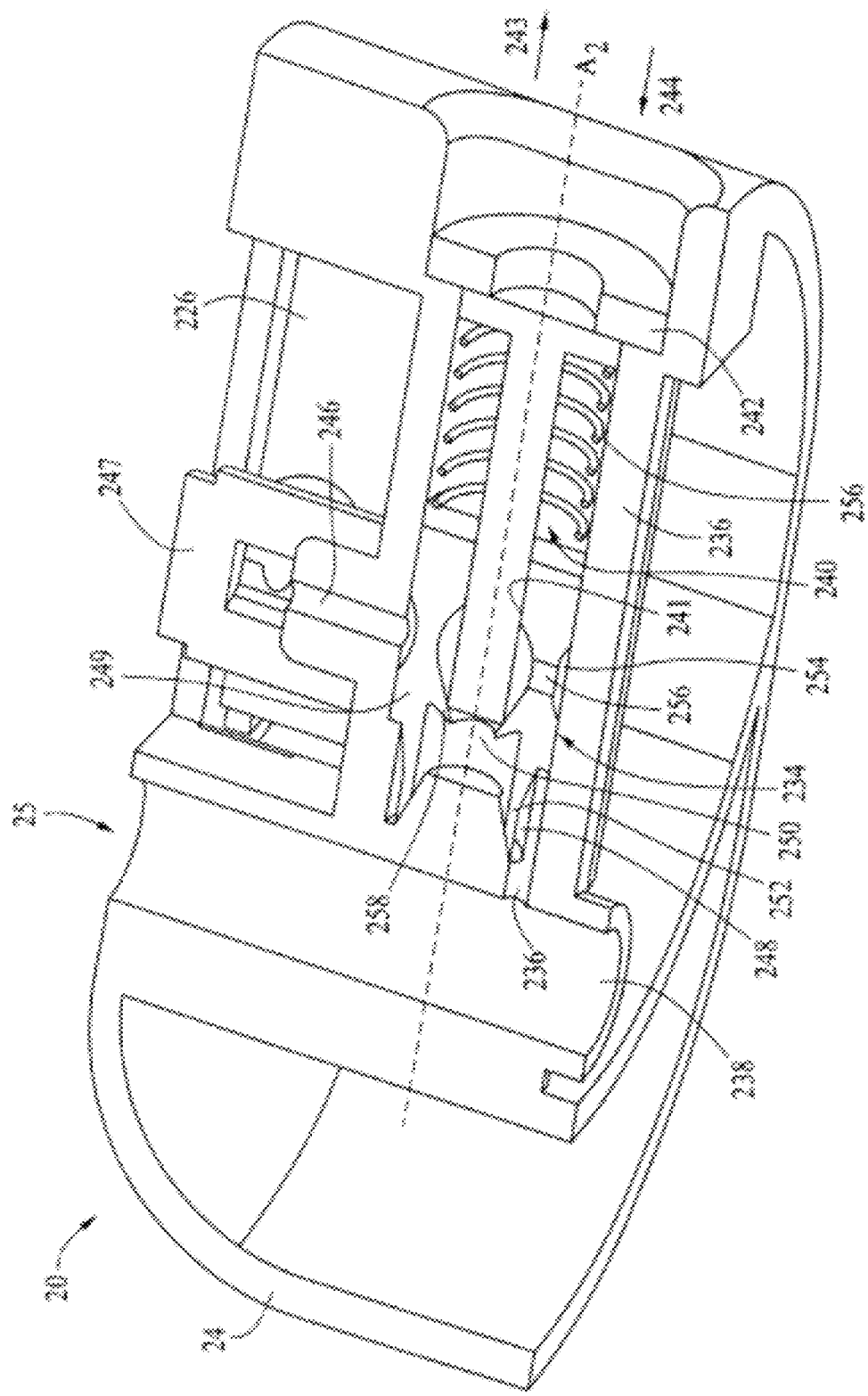

A linear-motion pump device 234 according to a further embodiment of the invention is shown in FIGS. 16 and 17. The pump device 234 may be located in the reservoir containing portion 24 of a disposable housing portion 20 as described above with respect to FIGS. 2 and 3. For example, the pump device 234 may be employed in a delivery device 12 as described above with respect to FIGS. 4-7, in place of the linear motion pump device 34 described above.

In FIGS. 16 and 17, the pump device 234 is operably connected to communicate fluid between a reservoir 226 in the reservoir containing portion 24 and an injection site 238. For example, the pump device 234 may be operated to communicate a fluidic infusion medium from the reservoir 226, to a patient, through a hollow needle or cannula inserted into the patient's skin at the injection site 238. A needle insertion mechanism (not shown in FIGS. 16 and 17) may be located within the injection site 238 and/or may be operated through an opening 25 (or other suitable operator) in the reservoir containing portion 24, as described above with respect to FIGS. 2 and 3. The reservoir 226 and injection site 238 in FIGS. 16 and 17 may be similar to the reservoir 26 and injection site 38 described above with respect to the embodiment of FIGS. 4-7.

The pump device 234 includes a piston 240 that is moveable in a longitudinal axial dimension $A_2$ of a piston channel 241. The piston 240 has a head portion 242 that may be arranged to be engaged by a drive shaft (such as drive shaft 84 of FIGS. 6 and 7) and/or connected to the drive shaft (for example, with a connection structure as described above with respect to the structure for connecting the drive shaft 84 to the piston section 148 of FIGS. 10-15), when the disposable housing portion 20 is engaged with and connected to the durable housing portion 22, as described above. By engagement and/or connection of the drive shaft 84 to the piston head 242, a drive device 82 in the durable housing portion 22 may be operated to control selective motion of the drive shaft 84 and, thus, the piston 240 in the axial dimension $A_2$, in the direction of arrows 243 and 244.

The piston 240 may be made of any suitably rigid material, including, but not limited to metal, plastic, ceramic, composite material or the like. In the embodiment of FIGS. 16 and 17, the disposable housing portion 20 includes a housing section 236 that defines a longitudinal channel in which the piston channel 241 and piston 240 are located. An inlet port 246, for example, an opening through the housing section 236, is provided in fluid flow communication with the reservoir 226 through a septum member 247. The septum member 247 may be made of a pierceable material, such as, but not limited to, a silicone, or other soft plastic material that may be pierced by a needle, and reseal itself after removal of the needle. The septum member 247 may be exposed through an opening in the disposable housing portion 20, for example, to allow refilling of the reservoir by piercing the septum with a syringe needle and expelling fluid from the syringe needle.

In FIGS. 16 and 17, a piston channel member 249 is located within the housing section 236 and has a central channel that defines the piston channel 241 and a piston chamber 250. A gap provided between a portion of the piston channel member 249 and a portion of the housing section 236 forms an outlet chamber 248. A one-way valve 252 is provided between the piston chamber 250 and the outlet chamber 248, to allow fluid flow from the piston chamber 250 to the outlet chamber 248 when fluid pressure within the piston chamber 250 is sufficient to open the one-way valve 252.

The piston channel member 249 has an annular channel 254 around its outer peripheral surface, in alignment and fluid flow communication with the inlet port 246. A further flow passage 256 in the piston channel member 249 connects the annular channel 254 in fluid flow communication with an piston chamber 250. The piston channel member 246 may be made of any suitably rigid material, including, but not limited to metal, plastic, ceramic, composite material or the like. For ease of manufacture, the piston channel member 246 may be formed as a separate member relative to the disposable housing portion 20 and may be secured to the disposable housing portion 20, within the central channel of the housing section 236, by any suitable connection mechanism including, but not limited to, a friction fit, adhesive, thermal bonding, or the like. In further embodiments, the piston channel member 246 may be formed unitarily with the housing section 236 of the disposable housing portion 20.

The piston 240 is moveable within the piston channel 241 along the axial dimension $A_2$, between an extended position (FIG. 16) and a retracted position (FIG. 17). A bias member, such as, but not limited to, a coil spring 257 may be provided to urge the piston in the direction of arrow 243, toward a retracted position. In the extended position (shown in FIG. 16), the piston abuts a piston valve seat 258 to inhibit fluid back-flow from the piston chamber 250, toward the passage 256 and annular channel 241. When the piston is in the retracted position (shown in FIG. 17), the piston is separated from the piston valve seat 258 and allows fluid to flow from the passage 256, into the piston chamber 250. The piston valve seat 258 may be formed as a unitary portion of the piston channel member 249 as shown in FIGS. 16 and 17, or may be formed separate from and connected to the piston channel member 249 during manufacture.

In operation, the piston 240 is moved axially, in the direction of arrow 243 to create a low pressure volume in the piston chamber 250 sufficient to draw fluid into the piston chamber 250, from the reservoir 226, through the inlet port 246, channel 241 and passage 256. Infusion medium from the reservoir may, thereby, enter and be contained in the piston chamber 250, until the piston 240 is moved in the direction of arrow 244. Once the piston chamber 250 is sufficiently filled with infusion medium, the piston 240 is moved in the direction of arrow 244, to increase the fluid pressure within the piston chamber 250. Once the fluid in the piston chamber 250 reaches a sufficient pressure, the one-way valve 252 opens and fluid in the chamber 250 passes from the chamber 250, to a conduit 236 that is connected in fluid flow communication with the injection site 238. The conduit 236 and injection site 238 may be similar to the conduit 36 and injection site 38 described above with respect to FIG. 4. The one-way valve 252 allows fluid to flow from the piston chamber 250 and out through the outlet chamber 248, but inhibits fluid flow from the outlet chamber 248 into the piston chamber 250.

In the embodiment of FIGS. 16 and 17, the one-way valve 252 includes a duckbill valve structure formed on the piston channel member. However, other embodiments may employ other suitable one-way valve configurations. Accordingly, as a result of the piston stroke in the direction of arrow 243 and then in the direction of arrow 244, a volume of infusion medium is drawn into the pump device 234 from a reservoir 226 and is then dispensed through the one-way valve 252, to an injection site 238, under the controlled motion of a drive device (such as, but not limited to, the drive shaft 84 and drive device 82 described above). Upon completion of the piston stroke in the direction of arrow 243 and then in the direction of arrow 244, the piston motion may be repeated, to cause further delivery of infusion medium to the injection site.

Accordingly, the pump device 234 of FIGS. 16 and 17 may be operated with the generally linearly moveable drive shaft 84, similar to the operation of the drive shaft 84 on the pump device 34 and 134, described above. Also, the pump device 234 of FIGS. 16 and 17 may be supported by a first housing portion (such as the disposable housing portion 20), while the drive shaft 84 and drive device 82 are supported by a second housing portion (such as the durable housing portion 22), where the first and second housing portions are configured to be selectively engaged for operation and disengaged from each other, as described above.

A linear-motion pump device 334 according to a further embodiment of the invention is shown in FIGS. 18-20. The pump device 334 of FIGS. 18-20 may be located in the reservoir containing portion 24 of a disposable housing portion 20 as described above with respect to FIGS. 2 and 3. For example, the pump device 334 may be employed in a delivery device 12 as described above with respect to FIGS. 4-7, in place of the linear motion pump device 34 and reservoir 26 described above.

The pump device 334 employs a miniature piezoelectric actuator or motor, for example, but not limited to the type referred to as a Squiggle motor (SQUIGGLE is a Trademark of New Scale Technologies), produced by New Scale Technologies, Inc. of Victor, N.Y. A representation of a miniature piezoelectric motor 344, such as a Squiggle motor, is shown in FIG. 18. With reference to FIG. 18, the motor 344 includes a support structure 345, such as a plate made of a suitably rigid material, such as, but not limited to, metal, plastic, ceramic, glass, composite material or the like. A piezoelectric patch or stack 346 is supported on one side of the support plate 345. A screw housing 347 is located on the opposite side of the piezoelectric patch or stack 346, relative to the support plate 345. The screw housing 347 may include, but is not limited to, a nut or plate having an opening through which a drive screw 348 extends. The screw housing 347 may be made of a suitably rigid material, such as, but not limited to, metal, plastic, ceramic, glass, composite material or the like. The threaded drive screw 348 extends through the screw housing 347, piezoelectric patch or stack 346 and motor support 345, and is arranged to move in a linear direction (of the arrow 349) and rotate relative to the screw housing 347 and motor support 345, upon actuation of the piezoelectric patch or stack 346. The piezoelectric patch or stack 346 is connected to a suitable power source and control electronics (not shown in FIG. 18), for selective energization of the piezoelectric patch or stack 346. The motor 344 may be supported in a durable housing portion 22, as described above. As the main body of the motor 344 vibrates, a screw is turned, resulting in linear motion that can be precisely controlled to a nanometer resolution. In one embodiment, the motor 344 is arranged as a linear actuator, where the screw is held stationary and the vibration generating portion is used to provide a force to push against a piston plunger in a reservoir to drive a fluid from the reservoir.

When the durable housing portion 22 is engaged with a disposable housing portion 20, the pump device 334 is operably connected to communicate fluid between a reservoir 326 in the reservoir containing portion 24 of the disposable housing portion and an injection site 338 (similar to the injection site 38 described above). The reservoir 326 may comprise a canister-style container or other suitable container that has an interior volume with a longitudinal dimension $A_2$ along which a piston plunger may move. The pump device 334 includes a piston plunger 336 that is located within the reservoir 326 and moveable in the longitudinal dimension $A_2$ of the reservoir 326. The piston plunger 336 includes a piston head 341 and a piston shaft 339. The piston head 341 has a shape and size suitable for sealing against the interior surface of the reservoir 326, to inhibit fluid flow between the piston head 341 and the interior surface of the reservoir 326. Alternatively, or in addition, one or more seals may be provided around the peripheral surface of the piston head 341, to inhibit fluid flow between the piston head 341 and the interior surface of the reservoir 326. Movement of the piston 336 in the direction of arrow 350 causes a fluid-containing portion 352 of the reservoir 326 to decrease in volume and drive fluid from the reservoir 326, to the injection site 338.

In the embodiment of FIGS. 19 and 20, the piston shaft 339 has a semi-cylindrical shape and an open, semi-cylindrical hollow interior section that is arranged to fit over and receive at least a portion of the motor 344 and to engage the motor support 345 of the motor 344, when the durable housing portion and the disposable housing portion are engaged. The semi-cylindrical piston shaft 339 may include suitably shaped indentations, cut-outs, openings or the like, to accommodate a portion of the motor 344, up to the screw housing 347. Further indentations, cut-outs or openings may be provided on the end surface of the semi-cylindrical piston shaft 339 to snugly mate with the screw housing 347 of the motor 344, Once the motor 344 is engaged with the piston shaft 339, the motor may be activated to prime the fluid path and to seat the motor on the piston shaft 339.

In the embodiment of FIG. 19, actuation of the motor 344 (by selective application of a controlled electrical power signal to the piezoelectric patch or stack 346) causes a relative motion between the drive screw 348 and the screw housing 347. By supporting one end of the drive screw 348 in engagement with a stationary surface 358 (stationary with respect to the durable housing portion), the relative motion of between the drive screw 348 and the screw housing 347 translates to a motion of the screw housing 347 in the direction of arrow 350. Because the screw housing 347 is engaged with the semi-cylindrical piston shaft 339, the motion of the screw housing 347 in the direction of arrow 350 causes the piston 336 to move in the direction of arrow 350. In this manner, a controlled activation of the piezoelectric patch or stack 346 provides a controlled motion of the piston 336 to selectively drive fluid from the reservoir interior 352, to the injection site 338. A frictionless bearing may be provided at the engagement location of the screw 348 and the surface 358. The hollow interior of the semi-cylindrical piston shaft 339 may be made sufficiently large to provide clearance to avoid obstructing any rotational motion of the drive screw 348.

Another embodiment as shown in FIG. 21 includes a reservoir 326 and a piston head 341 as described above with respect to FIG. 19. However, instead of employing a semi-cylindrical piston shaft (as described above with respect to FIG. 19), the embodiment in FIG. 21 employs the drive screw 348 of the motor 344 as the piston shaft, wherein one end of the drive screw 348 is connectable directly to the piston head 341 when the durable housing portion 22 is engaged with the disposable housing portion 20. Alternatively, an extension member may extend from the drive screw 348 and connect to the piston head 341, when the durable housing portion 22 is engaged with the disposable housing portion 20. In the embodiment in FIG. 21, the motor support 345 and/or the screw housing 347 of the motor 344 is (are) secured in a fixed relation to the durable housing portion 22, for example, by coupling one or both of those structures to a wall 360 of or in the durable housing portion 22. In operation, upon selective application of a suitable power signal to the motor 344, the drive screw 348 is caused to selectively move in the linear direction of arrow 350, to selectively move the piston head 341 relative to the reservoir 326. In this manner, the piston head 341 in FIG. 21 may be selectively moved to reduce the volume 352 of the interior of the reservoir 326 and drive fluid from the reservoir 326 to the injection site 338.

In embodiments described above, the disposable housing portion (e.g., 20 in FIG. 3) is provided with a base portion 21 that may be secured to the patient-user's skin by, for example, but not limited to, an adhesive material provided on the bottom surface of the base portion 21. That arrangement is generally represented, in side view, in FIG. 18, wherein an adhesive material 101 is provided on the bottom surface (skin-facing surface) of the base 21 of the disposable housing portion 20. As shown in FIGS. 2, 3 and 18, the durable housing portion 22 may be configure to be arranged on the base 21 of the disposable housing portion 20 to engage and connect to the disposable housing portion 20. In such an arrangement, the base 21 may be disposed between the durable housing portion 22 and the patient-user's skin, during operation, such that only the base 21 of the disposable housing portion remains in contact with the patient-user's skin, during operation.

However, in other embodiments, the durable housing portion 22 and the disposable housing portion 20 may be configured to engage each other in a side-by-side arrangement, for example, as represented in FIG. 19. In the side-by-side arrangement in FIG. 19, either one or both of the durable housing portion 22 and the disposable housing portion 20 may be provided with a base having an adhesive material 101 (and a peelable cover layer 23 as shown in FIG. 3).

In yet further embodiments, as represented by FIG. 20, one or both of the durable housing portion 22 and the disposable housing portion 20 may be attachable and detachable from a separate base member 21'. Suitable connecting structure, such as described above for connecting the durable housing portion and the disposable housing portion together, may be employed for connecting the durable housing portion and the disposable housing portion to the base member 21'. The separate base member 21' may include a generally flat, plate-like structure made of any suitably rigid material including, but not limited to, plastic, metal, ceramic, composite material or the like. The base member 21' has a surface (the upper-facing surface in FIG. 20) to which the disposable housing portion 20 and the durable housing portion 22 may be attached. The base member 21' has a second surface (the lower-facing surface in FIG. 20) to which an adhesive material and a peelable cover film may be applied, as described above, to allow the base member 21' to be secured to a patient-user's skin.

The base member 21' may include a needle inserter device 25, as described above. Examples of suitable needle inserter devices are described in U.S. patent application Ser. No. 11/211,095, filed Aug. 23, 2005, and U.S. Patent Application No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, each of which is incorporated herein by reference in its entirety. In such embodiments, the base member 21' may be secured to a patient-user's skin. Then, the needle inserter 25 may be activated to insert a hollow needle or cannula into the patient-user's skin. Then, after the hollow needle or cannula is inserted, the durable housing portion 22 and the disposable housing portion 20 may be attached to the base member 21', to connect the reservoir within the disposable housing portion 20 in fluid flow communication with the hollow needle or cannula. In one embodiment, the durable housing portion 22 and the disposable housing portion 20 may be connected together (for example, in the manner described above) before attaching those housing portions to the base member 21'. In a further embodiment, one of the durable and disposable housing portion is attached to the base member 21' before the durable and disposable housing portions are connected together. In such further embodiment, the needle inserter device may be activated to insert a hollow needle or cannula into the patient-user's skin after the disposable housing portion is attached to the base member 21' (either before or after the durable and disposable housing portions are connected together). Other needle/cannula insertion tools may be used (or modified for use) to insert a needle and/or cannula, such as for example U.S. patent application Ser. No. 10/389,132 filed Mar. 14, 2003, and entitled "Auto Insertion Device For Silhouette Or Similar Products," and/or U.S. patent application Ser. No. 10/314,653 filed Dec. 9, 2002, and entitled "Insertion Device For Insertion Set and Method of Using the Same," both of which are incorporated herein by reference in their entirety.

Alternatively, reference number 25 may represent an opening in the base member 21' that aligns with a needle inserter device (or aligns with a further opening) located in the disposable housing portion 20, when the disposable housing portion 20 is attached to the base member 21'. In such embodiments, the base member 21' may be secured to the patient-user's skin. Then the disposable housing portion 20 is attached to the base member 21' (either before or after the durable and disposable housing portions are connected together). Once the disposable housing portion 20 is attached to the base member 21', the needle inserter device 25 may be activated to insert a hollow needle or cannula into a patient-user's skin (either before or after the durable and disposable housing portions are connected together).

Also, while embodiments described above may include an on-board needle or cannula injector device that may be activated through the operator or opening 25, other embodiments may employ an injection site module 103 that is external to the disposable housing portion 20, but connected to the disposable housing portion 20, through a suitable conduit 102, as shown in FIG. 21. The external injection site module 103 may include a needle or cannula injector device structure and an operator or opening (similar to the operator or opening 25 described above) through which the injector device may be activated. Alternatively or in addition, the external injection site module 103 may include an infusion set such as, but not limited to an infusion set as described or referenced in U.S. patent application Ser. No. 10/705,686, filed Nov. 10, 2003, titled "Subcutaneous Infusion Set" (Publication No. 2005/0101910) and/or U.S. patent application Ser. No. 11/004,594, filed Dec. 3, 2004, titled "Multi-Position Infusion Set Device And Process" (Publication No. 2006/0129090), each of which is assigned to the assignee of the present invention and each of which is incorporated herein by reference, in its entirety.

The conduit 102 that connects the module 103 with the disposable housing portion 20 may be any suitable tubing structure having a fluid flow passage, such as, but not limited to, a flexible tube made of plastic, silicone or the like. An adhesive material may be provided on the tubing structure (or between the tubing structure and the patient-user's skin) to secure the tubing to the patient-user's skin. By locating the injection site module 103 external to the disposable housing portion 20, the disposable housing portion 20 and the durable housing portion 22 may be clipped to a patient-user's clothing, belt, suspender or other article of apparel or may be held in a pocket of an article of apparel or carried in a purse or the like.

In one embodiment, the conduit 102 may be fixed at one end to the disposable housing portion 20, in fluid-flow communication with the reservoir within the disposable housing portion 20, and fixed at a second end to an external injection site module 103, for connection in fluid-flow communication with a hollow needle or cannula, as described above. In further embodiments, one or both of the ends of the conduit 102 may include suitable connection structures that allow the conduit ends to be selectively connected in fluid-flow communication with, and selectively disconnected from the disposable housing portion 20 and/or the injection site module 103. Such connectors may comprise a hollow needle and septum, a Luer connector, or other suitable fluid-communication connectors. In such embodiments, the disposable housing portion 20 and the durable housing portion 22 may be disconnected from the module 103, for example, by disconnecting one of the ends of the conduit 102 from the module 103 or the disposable housing portion 20, while leaving the module 103 in place (without requiring the patient-user to withdraw the needle or cannula and, later, insert a needle or cannula to resume operation). In this manner, a patient-user may readily disconnect and remove the disposable housing portion 20 and durable housing portion 22, for example, to allow the patient-user to shower, bath, swim or conduct other activities, yet also allow the patient-user to readily re-connect the disposable housing portion 20 to the module 103, for example, upon completion of such activities. Examples of connectors can be found in U.S. patent application Ser. No. 10/328,393 filed Dec. 22, 2003, and entitled "Reservoir Connector," and U.S. Pat. No. 5,545,152 issued Aug. 13, 1996, and entitled "Quick-Connect Coupling For A Medication Infusion System," both of which are incorporated herein by reference in their entirety. In other alternatives, different connectors such as Luer locks, or the like may be used.

Figure 22:
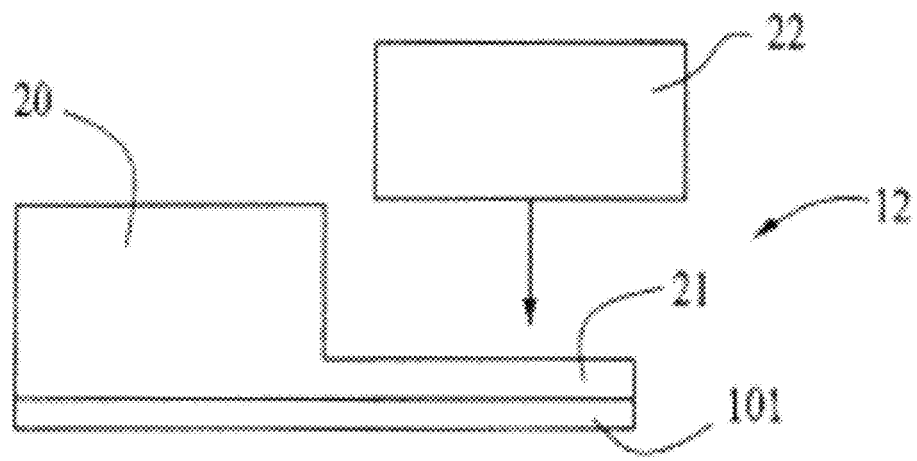
FIG. 22 shows a schematic side view of an arrangement of a durable housing portion and a disposable housing portion of a delivery system according to an embodiment of the invention consistent with the embodiment of FIG. 3.

In yet further embodiments, the conduit 102 may be eliminated and an injection site module 103 may be directly connected with the disposable housing portion 20, as shown in FIG. 22. In such an embodiment, one or more suitable fluid flow passages are provided through the disposable housing portion 20 and into the injection site module 103, for fluid-flow communication between the reservoir in the disposable housing portion 20 and a hollow needle or cannula, as described above. Also, in such embodiments, the injection site module 103 and the disposable housing portion 20 may include mating connection structures to allow the injection site module 103 and the disposable housing portion 20 to be selectively connected and disconnected from each other.

Various examples of mating arrangements, for directly connecting an injection site module 103 to a disposable housing portion are described with reference to FIGS. 23-30. FIGS. 23-30 show an example arrangement, in which an injection site module 103 includes at least one (two in FIG. 23) protruding engagement pawl 174 that are configured to be received in a corresponding number of receptacles on the disposable housing portion 20 (similar to the pawls 74 and receptacles 76 described above). In other embodiments, the pawl(s) 174 may be located on the disposable housing portion 20, while the corresponding receptacles may be located on the module 103. In yet other embodiments, each of the disposable housing portion 20 and the module 103 may include one or more pawls and one or more receptacles.

Figure 23:
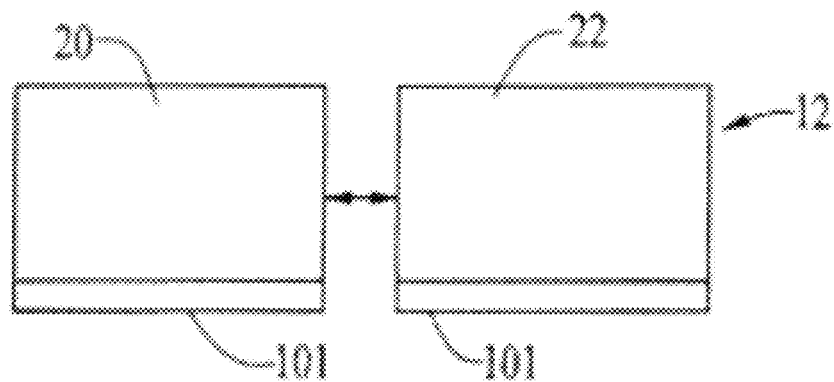
FIG. 23 shows a schematic side view of an arrangement of a durable housing portion and a disposable housing portion of a delivery system according to another embodiment of the invention.
Figure 24:
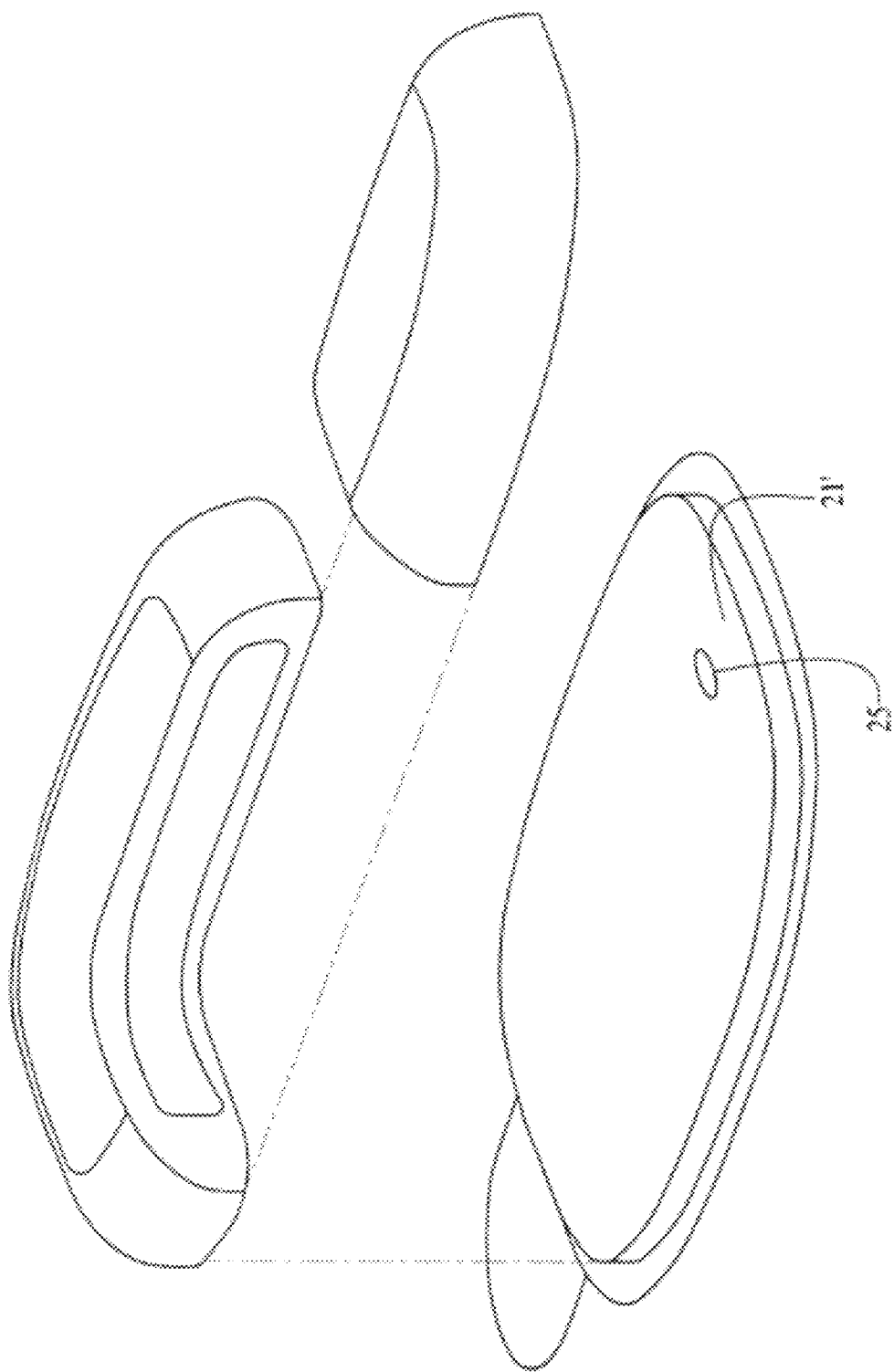
FIG. 24 shows a partially exploded view of a delivery device according to an embodiment of the invention.
Figure 25:
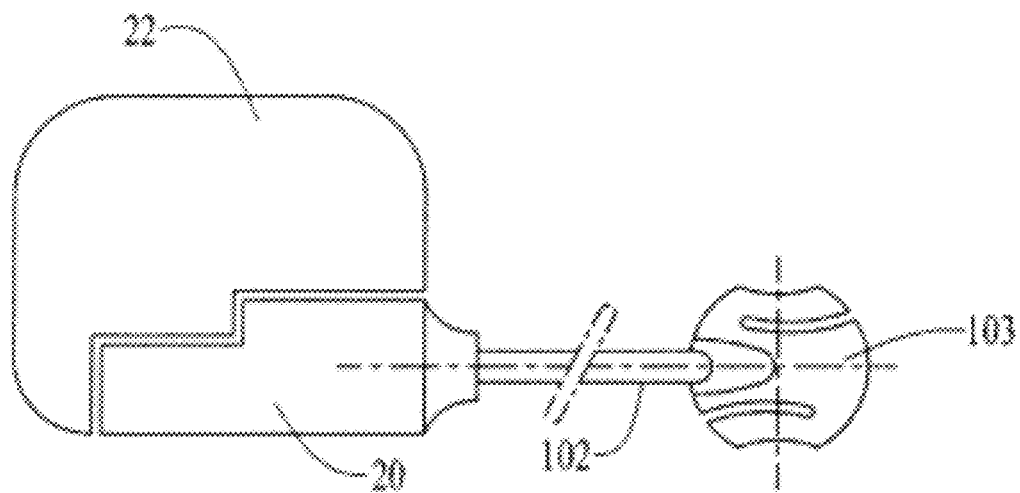
FIG. 25 shows a schematic top view of an arrangement of a durable housing portion and a disposable housing portion of a delivery system according to an embodiment of the invention.

The pawls 174 and receptacles may be configured to allow a patient-user to manually slide the pawls into the receptacles as the disposable housing portion 20 and the module 103 are brought together. When the pawls 174 are received in the corresponding receptacles, the module 103 is secured to the disposable housing portion 20. The pawls 174 may include a shaped portion or head to provide a snap-fit with the receptacles, when the pawls 174 are fully received within the receptacles. The pawls 174 may be configured with sufficient flexibility to allow the patient-user to separate the disposable housing portion 20 from the module 103, by applying a sufficient force to full those two parts away from each other and unsnap the pawls 174 from the receptacles. In the embodiment of FIGS. 23-25, the module 103 may be attached to or may include a base portion 450 that be secured to a patient-user's skin during operation, in lieu of the extended base 21 of the disposable housing portion 20 described above. The base portion 450 may include an adhesive material as described herein with respect to the base 21 of the disposable housing portion 20.

As shown in FIG. 25, the embodiment of FIGS. 23-25 may be formed in three general parts, including the disposable housing portion 20, the durable housing portion 22 and the module 103 on the base portion 450. The durable housing portion 22 and the disposable housing portion 20 may be secured together (as shown in FIG. 23), and the combined, connected disposable and durable housing portions may be secured to the module 103 and base portion 450. In one embodiment, the base portion 450 may be secured to a patient-user's skin, before the combined, connected disposable and durable housing portions are secured to the module 103 and base portion 450. In a further embodiment, the combined, connected disposable and durable housing portions are secured to the module 103 and base portion 450, before the base portion 450 is secured to the patient-user's skin.

Figure 26:
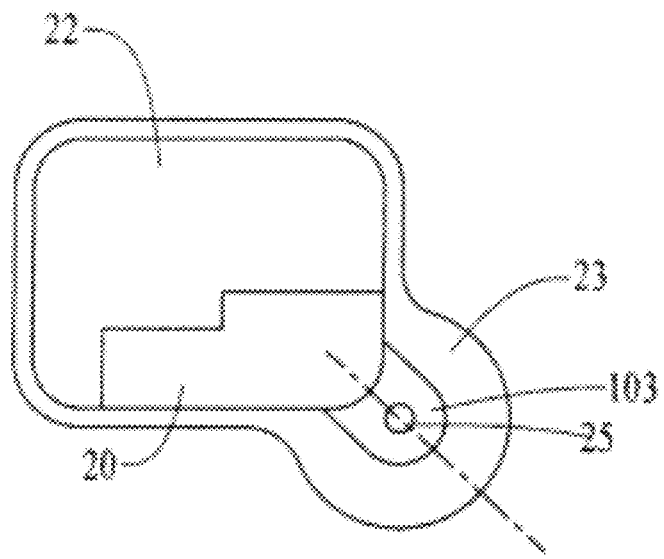
FIG. 26 shows a schematic top view of an arrangement of a durable housing portion and a disposable housing portion of a delivery system according to another embodiment of the invention.
Figure 27:
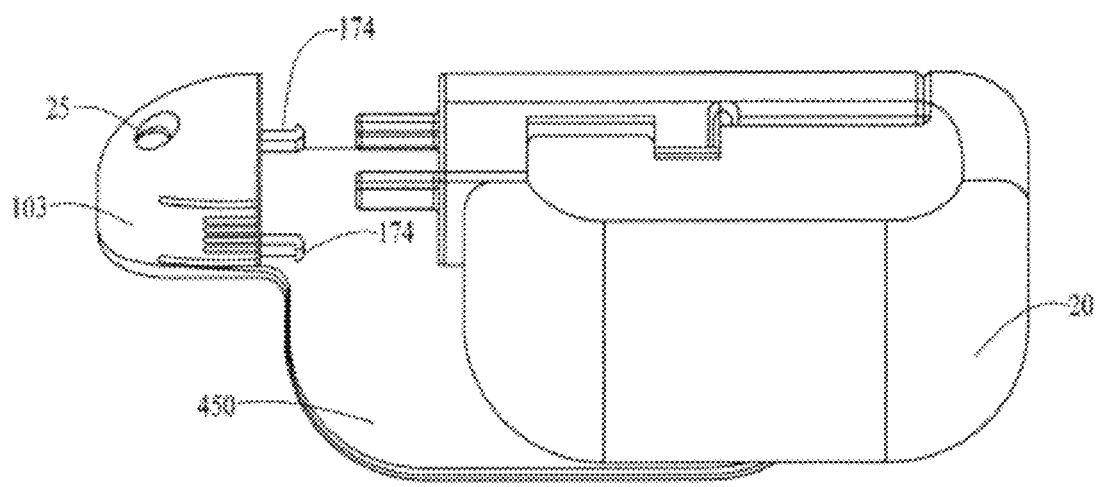
FIGS. 27-29 each show a perspective view of a connection arrangement for a disposable housing portion and an injection site module.

Another example of a connection structure is described with reference to FIGS. 26 and 27, wherein the module 103 includes a shaped head 452 configured to be received within a correspondingly shaped opening or receptacle in the disposable housing portion 20. The shaped head 452 may be configured with a shape that allows the head to be received in the receptacle when the disposable housing portion 20 is aligned relative to the module 103 in a first alignment position, as shown in FIG. 26, and further allows the disposable housing portion 20 to be rotated relative to the module 103 while the head 452 is received within the receptacle to a second alignment position as shown in FIG. 27. The receptacle in the disposable housing portion 20 may be shaped to allow the head 452 to be freely received or removed from the receptacle, when the disposable housing portion 20 is in the first alignment position (FIG. 26), yet abut the head 452 and inhibit separation of the head 452 from the receptacle (and, thus, inhibit separation of the disposable housing portion 20 from the module 103), when the disposable housing portion is in the second alignment position (FIG. 27).

Figure 28:
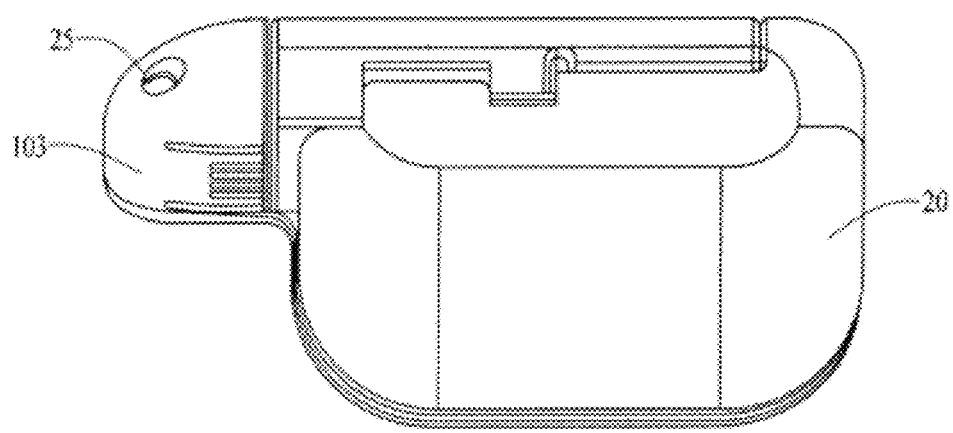
Figure 29:
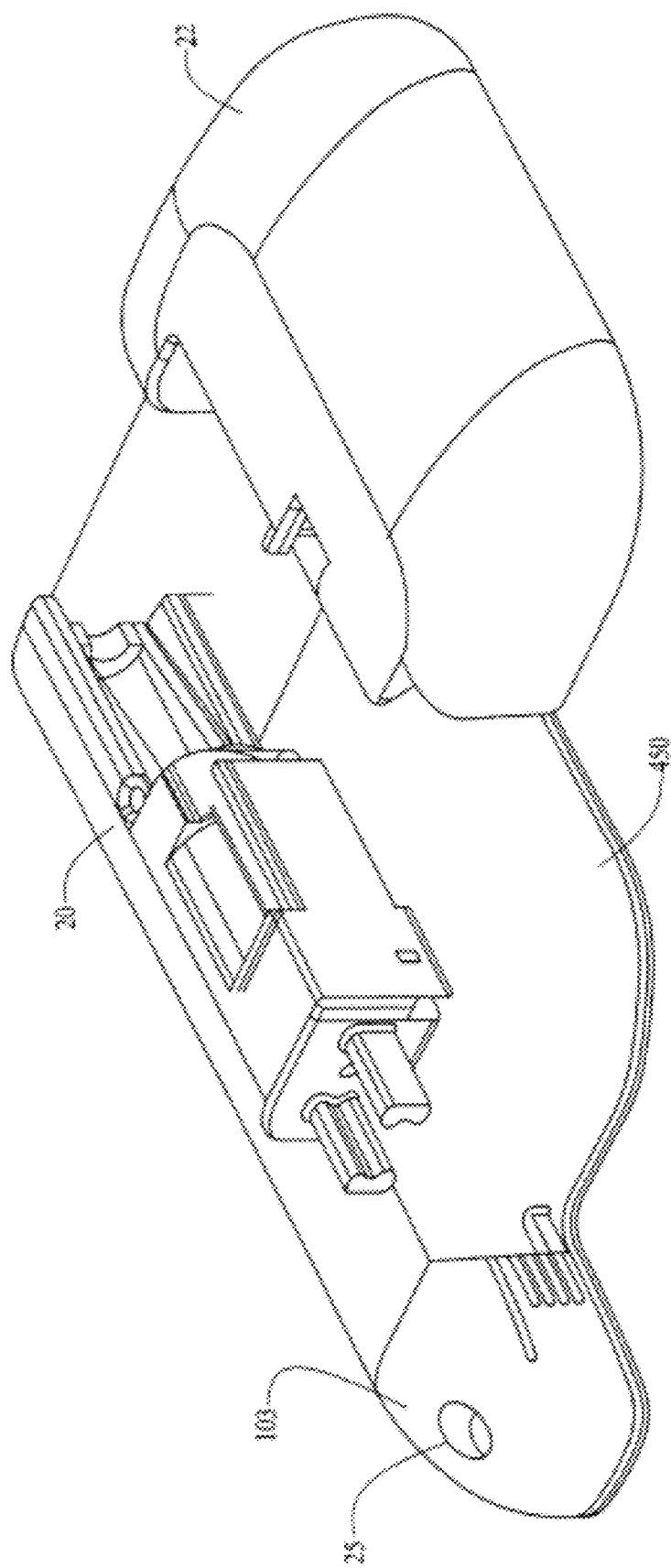
Figure 30:
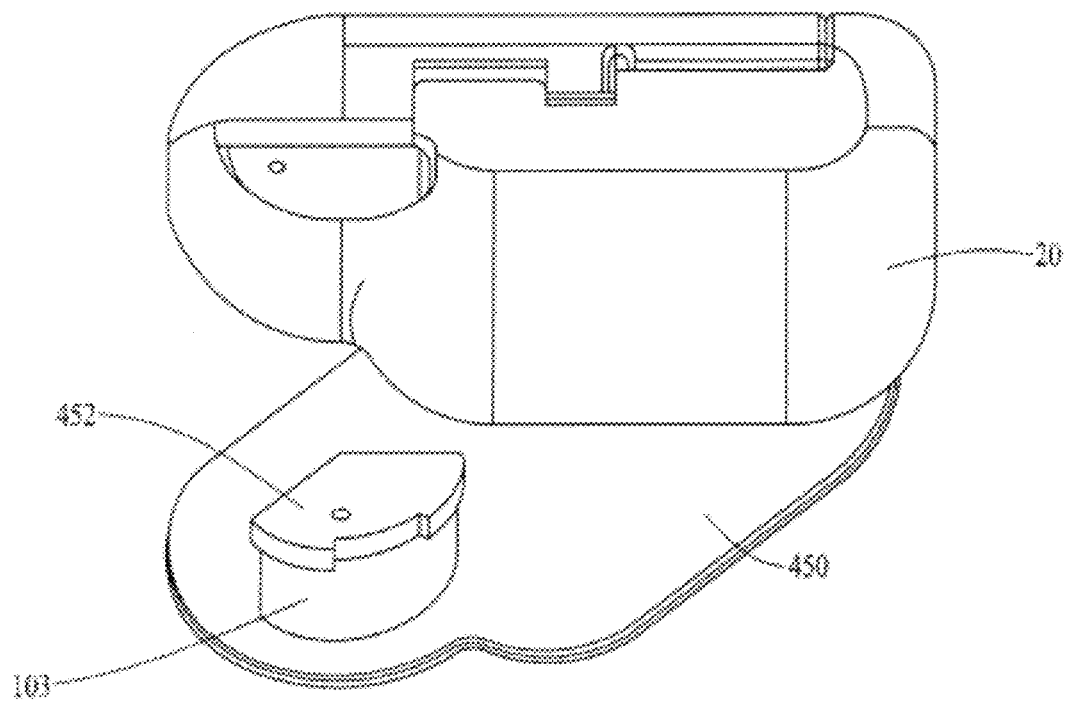
FIGS. 30 and 31 each show a perspective view of another connection arrangement for a disposable housing portion and an injection site module.
Figure 31:
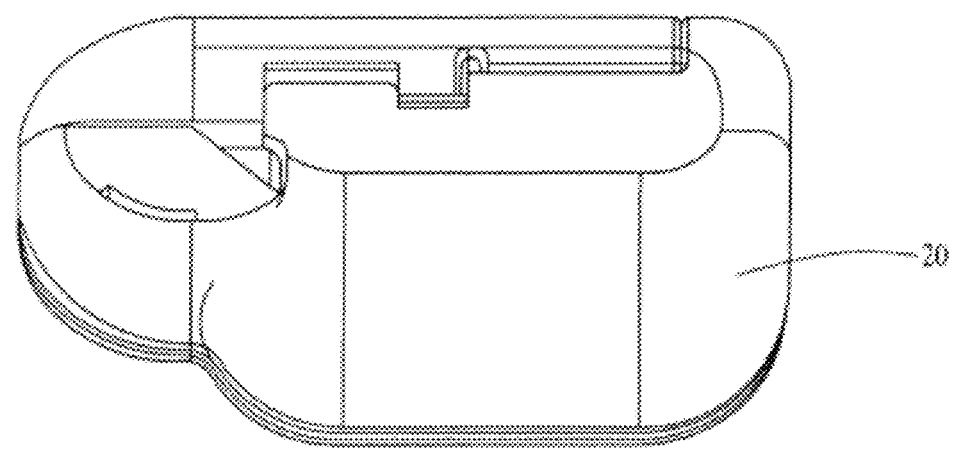
Figure 32:
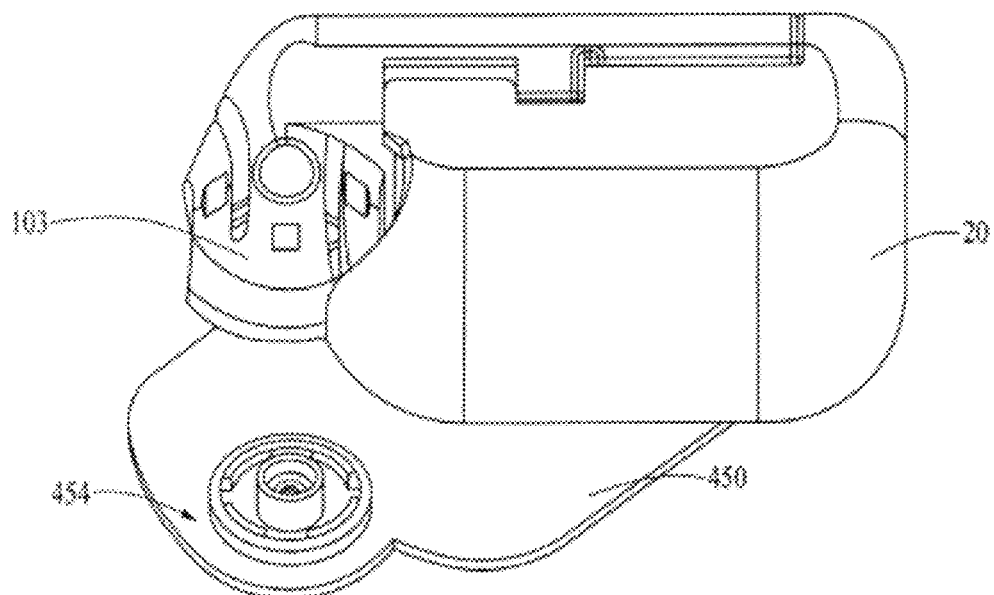
FIGS. 32-34 each show a perspective view of yet another connection arrangement for a disposable housing portion and an injection site module.
Figure 33:
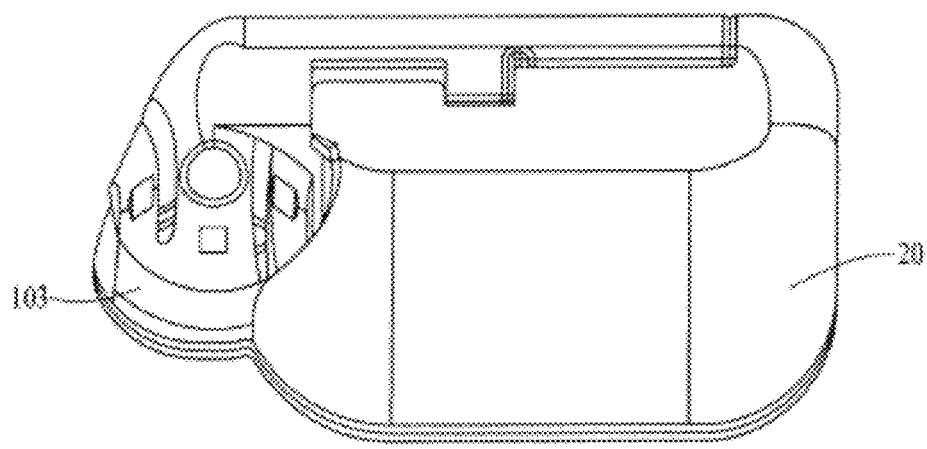
Figure 34:
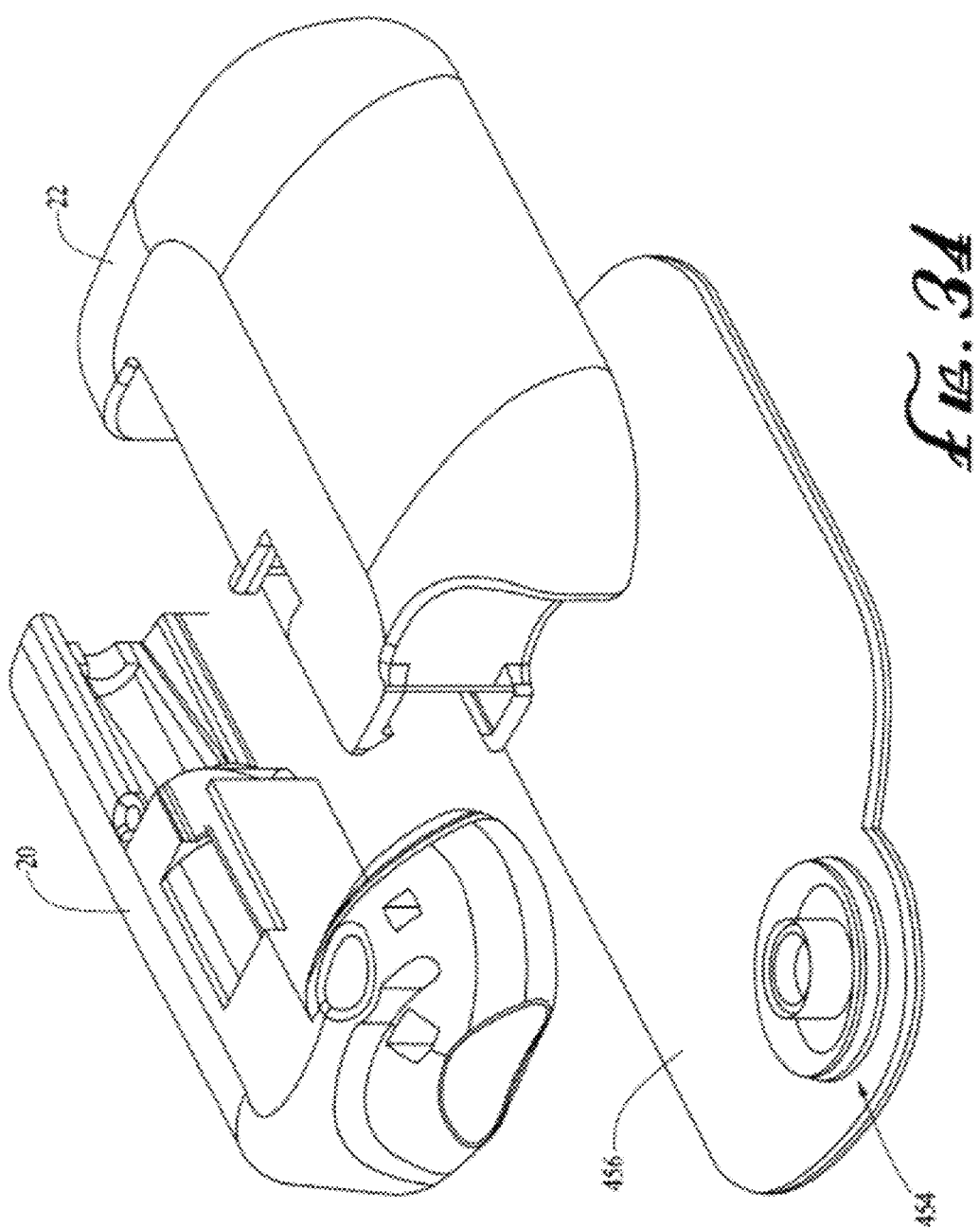

A further example of a connection structure is described with reference to FIGS. 28-30, wherein the module 103 includes a shaped receptacle 454 configured to receive a correspondingly shaped connector member in the disposable housing portion 20. In FIGS. 28-30, the module 103 is formed, integral with the disposable housing portion 20. The shaped receptacle 454 may be configured with a shape that allows the connector member of the disposable housing portion to be engaged with the receptacle 454 when the disposable housing portion 20 is aligned relative to the module 103 in a first alignment position, as shown in FIG. 28, and further allows the disposable housing portion 20 to be rotated relative to the module 103, while the receptacle 454 is engaged within the connector member, to a second alignment position as shown in FIG. 29. The receptacle 454 and the connector member in the disposable housing portion 20 may be shaped to allow the connector member to be freely engage the receptacle 454, when the disposable housing portion 20 is in the first alignment position (FIG. 28), yet lock with the receptacle 454 and inhibit separation of the connector member from the receptacle (and, thus, inhibit separation of the disposable housing portion 20 from the module 103), when the disposable housing portion is in the second alignment position (FIG. 29). The receptacle 454 and connection member may include any suitable known rotary connection structures for connecting two structures together upon engagement and relative rotation of the two structures in one direction, yet allow the two structures to be disengaged and separated from an engaged arrangement, by relative rotation of the two structures in the second, opposite direction.

As shown in FIG. 30, the embodiment of FIGS. 28-30 may be formed in three general parts, including the disposable housing portion 20, the durable housing portion 22 and the module 103 on the base portion 456. The durable housing portion 22 and the disposable housing portion 20 may be secured together (as shown in FIG. 28), and the combined, connected disposable and durable housing portions may be secured to the base portion 456. In one embodiment, the base portion 456 may be secured to a patient-user's skin, before the combined, connected disposable and durable housing portions are secured to the base portion 456. In a further embodiment, the combined, connected disposable and durable housing portions are secured to the base portion 456, before the base portion 456 is secured to the patient-user's skin.

In yet further embodiments, the injection site module may be formed as a unitary structure with the disposable housing portion 20. Also, in any of the embodiments described above, one or more sensors may be located in the disposable housing portion 20, the injection site module 103 or the durable housing portion 22, for sensing a biological condition, including, but not limited to, blood glucose level, level of infusion medium in the patient-user's blood and/or other conditions. Such sensor(s) may include a hollow needle or cannula and/or a set of micro-needles, as described above, for piercing the patient-user's skin to convey fluid from the patient to the sensor.

Also, while embodiments described above may include an adhesive material and a cover film 23 (FIGS. 2 and 3), further embodiments may include a plurality of adhesive material layers alternating with a corresponding plurality of cover film layers 23, to allow the delivery device to be secured, removed and re-secured to the patient-user's skin one or more times. In such embodiments, a first cover film layer located at the end of the stack of alternating layers of adhesive material and cover film, may be removed to expose a first layer of adhesive material. With the first layer of adhesive material exposed, the delivery device (or component thereof) may be adhered to a patient-user's skin, as described above. After a suitable period of usage, the delivery device (or component having the adhesive) may be removed from the patient-user's skin, for example, for servicing, re-filling, replacement of one or more components, or the like. After removal of the delivery device (or component) from the patient-user's skin, a second cover film layer on the delivery device (or component) may be removed to expose a second layer of adhesive material. With the second layer of adhesive material exposed, the delivery device (or component) may be secured to the same patient-user or, in certain contexts, to a different patient-user, for further operation. The process may be repeated a number of times up to the number of adhesive material and cover film layer pairs are included in the plural alternating layers of adhesive material and cover film.

In addition, while embodiments described above include an injection site located on the disposable housing portion 20 or in an external injection site module 103, other embodiments may employ an injection site located in the durable housing portion 22 and connected, through suitable fluid-flow passages, to the reservoir in the disposable housing portion 20, when the durable housing portion and disposable housing portion are engaged. Also, while embodiments are described above in the context of delivery devices for delivering an infusion medium from a reservoir to a patient-user, other embodiments may be operated to withdraw a fluidic medium from a patient-user (or other source) and transfer the fluidic medium to the reservoir. Such other embodiments may be operated by operating the drive device to selectively move the piston plunger away from the septum-end of the reservoir (to increase the fluid-retaining volume of the reservoir) to create a negative pressure sufficient to draw fluid from the patient-user (or other source) to which the hollow needle or cannula is secured.

Various aspects of the multiple embodiments described above may be employed independently or in combinations thereof. Significant advantages can be obtained from various embodiments and combinations described herein, wherein an at-site delivery system may be made of two parts, including a disposable portion and a non-disposable portion. The disposable portion may contain components that are in direct contact with the infusion medium, such as reservoir body, reservoir piston, septum systems and injection needle. The non-disposable portion could contain components that are not in contact with the medication including the drive system, pressure or force sensing system, battery, electronics, display, and non-disposable housing. By simplifying the manner in which the disposable portion of the delivery device can be replaced and by simplifying the manner in which the delivery device can be re-activated after replacing a disposable portion, a greater number of patients will be able to use and benefit from such delivery devices.

While particular embodiments of the present invention have been shown and described, it will be obvious to those skilled in the art that the invention is not limited to the particular embodiments shown and described and that changes and modifications may be made without departing from the spirit and scope of the claimed invention. For example, while embodiments are described above in the context of delivery devices for delivering an infusion medium from a reservoir to a patient-user, other embodiments may be operated to withdraw a fluidic medium from a patient-user (or other source) and transfer the fluidic medium to the reservoir. Such other embodiments may be operated to move fluid toward the reservoir, for example, by reversing the direction of the one-way valves 40 and 42.

What is claimed is:

1. A delivery device for delivering an infusion medium to a user, the device comprising:
   a first housing portion adapted to be secured to a user;
   a second housing portion configured to be selectively engaged with and disengaged from the first housing portion to allow disposal of the first housing portion without disposing of the second housing portion, the first housing portion having an enclosed interior volume;
   a drive shaft supported by the second housing portion when the second housing portion is selectively engaged with the first housing portion and when the second housing portion is disengaged from the first housing portion, for movement in a generally linear dimension;
   a drive device operatively connected to the drive shaft when the second housing portion is selectively engaged with the first housing portion and when the second housing portion is disengaged from the first housing portion, to selectively move the drive shaft in the generally linear dimension; and
   a pump device supported by the first housing portion, the pump device comprising:
   a housing provided with a piston channel having a generally linear, longitudinal axis extending along an axial dimension, the piston channel having an inlet port for connection to a reservoir, and the piston channel having an outlet for connection in fluid flow communication with an injection site, the inlet port being separated from the outlet port by a distance along the axial dimension of the piston channel axis;
   a piston located in the piston channel and having a first surface for receiving a drive force from the drive shaft when the first housing portion and the second housing portion are engaged, the piston having a second surface, and the piston having a generally linear, longitudinal axis extending along the longitudinal axis of the piston channel;
   wherein the piston is moveable in the piston channel with movement of the drive shaft along the longitudinal axis of the piston channel between fill and dispense positions, such that:
   in the fill position, the piston is moved to a position at which the second surface is laterally offset from the inlet port to allow fluid flow communication through the inlet port and into the piston channel;
   in the dispense position, the piston is moved to a position at which the second surface covers the inlet port to obstruct fluid flow communication through the inlet port and to force fluid in the piston channel out of the outlet port; and
   fluid that is allowed to flow through the inlet port into the piston channel is conveyed through the piston channel, in a direction of the longitudinal axis of the piston channel, to the outlet port by movement of the piston in the piston channel from the fill position to the dispense position.

2. A delivery device according to claim 1, wherein the pump device further comprises a one-way valve in fluid flow communication with the outlet port and arranged to allow fluid flow out from the piston channel through the outlet-port and inhibit fluid flow into the piston channel from the outlet port.

3. A delivery device according to claim 1, further comprising a reservoir having an interior volume for containing an infusion medium and a conduit connecting the interior volume of the reservoir in fluid flow communication with the inlet port of the housing of the pump device.

4. A delivery device according to claim 3, wherein the reservoir is supported by the first housing portion.

5. A delivery device according to claim 1, wherein:
the second housing portion comprises a housing structure having an interior volume in which the drive device is located,
the housing structure of the second housing portion includes a wall having an opening;
the drive shaft extends through the opening in the wall of the second housing portion.

6. A delivery device according to claim 5, wherein the drive shaft has an end that is positioned external to the second housing portion for operable connection with the surface of the piston, when the first housing portion and the durable second housing portion are engaged with each other.

7. A delivery device according to claim 1, wherein one of the first housing portion and the second housing portion has at least one flexible pawl and the other of the first housing portion and the second housing portion has at least one receptacle having a shape for receiving the at least one flexible pawl, when the first housing portion and the second housing portion are engaged with each other.

8. A delivery device according to claim 7, wherein each flexible pawl includes a first stop surface and each receptacle includes a second stop surface and wherein the first stop surface engages the second stop surface, upon the pawl being received within the receptacle.

9. A delivery device according to claim 1, further comprising electrical control circuitry contained in the second housing portion, wherein the electrical control circuitry controls the drive device for delivery of the infusion medium from the reservoir to the user when the first housing portion and the second housing portion are engaged.

10. A delivery device according to claim 1, wherein the first housing portion comprises a base portion having a bottom surface and an adhesive material on the bottom surface for securing the first housing portion to the skin of the user.

11. A delivery device according to claim 1, wherein the first housing portion comprises a base portion having a bottom surface securable to the skin of the user, the delivery device further comprising an injection site at which a hollow needle or cannula may be inserted into a user's skin when the bottom surface of the base portion is secured to the user's skin, and a conduit coupling the injection site in fluid flow communication with the outlet port of the pump device.

12. A delivery device according to claim 11, further comprising a one-way valve within the conduit.

13. A delivery device according to claim 1, further comprising a conduit coupled to the inlet port of the pump device, and a one-way valve within the conduit.

14. A delivery device according to claim 1,
the drive shaft having a first end for operatively communicating with the surface of the piston when the first housing portion and the second housing portion are engaged;
the first end of the drive shaft arranged to be out of operative communication with the surface of the piston when the first housing portion and the second housing portion are disengaged.

15. A delivery device according to claim 14, the drive shaft having a second end located within the second housing portion and operatively coupled to the drive device within the second housing portion.

16. A delivery device according to claim 1,
the drive shaft having a first end for engaging the surface of the piston when the first housing portion and the second housing portion are engaged;
the first end of the drive shaft arranged to be disengaged from the surface of the piston when the first housing portion and the second housing portion are disengaged.

17. A delivery device according to claim 1,
the drive shaft comprising a shaft having a constant linear dimension along a longitudinal axis and supported for movement along the longitudinal axis of the shaft.

18. A delivery device according to claim 1,
the drive shaft extending through an opening of the second housing portion and having one end within an interior of the second housing portion and a second end outside of the second housing portion.

19. A delivery device according to claim 1,
the drive shaft coupled to a rotational motion producing device.

20. A delivery device according to claim 1, wherein the housing is made of a generally rigid material that maintains a constant shape as the piston is moved from the fill position to the dispense position.

21. A pump device for conveying a fluidic medium, the pump device comprising:
a housing provided with a piston channel having a generally linear, longitudinal axis extending along an axial dimension, the piston channel having an inlet port for connection to a reservoir, and the piston channel having an outlet port for connection in fluid flow communication with an injection site, the inlet port being separated from the outlet port by a distance along the axial dimension of the piston channel axis; and
a piston located in the piston channel and having a first surface for receiving a drive force from a drive shaft, the piston having a second surface, and the piston having a generally linear, longitudinal axis extending along the longitudinal axis of the piston channel;
wherein the piston is moveable in the piston channel and along the longitudinal axis of the piston channel between fill and dispense positions upon receiving a force from a drive shaft, such that:
in the fill position, the piston is moved to a position at which the second surface is laterally offset from the inlet port to allow fluid flow communication through the inlet port and into the piston channel;
in the dispense position, the piston is moved to a position at which the second surface covers the inlet port to obstruct fluid flow communication through the inlet port and to force fluid in the piston channel out of the outlet port;
and fluid that is allowed to flow through the inlet port into the piston channel is conveyed through the piston channel, in a direction of the longitudinal axis of the piston channel, to the outlet port by movement of the piston in the piston channel from the fill position to the dispense position.

22. A pump device according to claim 21, wherein the pump device further comprises a one-way valve in fluid flow communication with the outlet port and arranged to allow fluid flow out from the piston channel through the outlet port and inhibit fluid flow into the piston channel from the outlet port.

23. A pump device according to claim 21, wherein the pump device is supported in a housing structure of an infusion delivery device having a drive device operatively coupled to the drive shaft for driving the drive shaft to apply the drive force to the surface of the piston.

24. A pump device according to claim 23, wherein the housing structure of the infusion delivery device comprises:
a disposable housing portion adapted to be secured to a user;
a durable housing portion configured to be selectively engaged with and disengaged from the disposable housing portion to allow disposal of the disposable housing portion without disposing of the durable housing portion, the durable housing portion having an enclosed interior volume;

wherein the pump device is supported by the disposable housing portion and the drive device is supported by the durable housing portion.

25. A pump device according to claim 24, wherein the drive shaft is supported by the durable housing portion.

26. A pump device according to claim 21, where the second surface of the piston has a generally cylindrical shape.

27. A pump device according to claim 21, where the second surface of the piston extends along the direction of the longitudinal axis of the piston channel.

28. A pump device according to claim 27, where the first surface of the piston extends along the direction transverse to the longitudinal axis of the piston channel.

29. A pump device according to claim 21, wherein the housing is made of a generally rigid material that maintains a constant shape as the piston is moved from the fill position to the dispense position.

30. A pump device according to claim 21, wherein the inlet port is configured for receiving fluid into the piston channel, the outlet port configured for conveying fluid out of the piston channel, the piston channel and piston configured to convey fluid in the axial dimension of the piston channel axis from the inlet port to the outlet port.

31. A method for delivering an infusion medium to a user, the method comprising:

providing a first housing portion and a second housing portion;

providing the first housing portion and the second housing portion with connection structure to allow the first housing portion and the second housing portion to be selectively engaged with each other for operation and disengaged from each other to allow disposal of the first housing portion without disposing of the second housing portion;

supporting a drive shaft with the second housing portion when the second housing portion is selectively engaged with the first housing portion and when the second housing portion is disengaged from the first housing portion, for movement in a generally linear dimension;

operatively connecting a drive device to the drive shaft when the second housing portion is selectively engaged with the first housing portion and when the second housing portion is disengaged from the first housing portion, to selectively move the drive shaft in the generally linear dimension;

supporting a pump housing with the first housing portion, the pump housing having a piston channel having a generally linear, longitudinal axis extending along an axial dimension;

providing the piston channel with an inlet port for connection to a source of fluidic medium;

providing the piston channel with an outlet port, the outlet port being separated from the inlet port by a distance along the axial dimension of the piston channel axis;

providing a piston having a first surface for receiving a drive force from the drive shaft when the first housing portion and the second housing portion are engaged for operation, the piston having a second surface, and the piston having a generally linear, longitudinal axis extending along the longitudinal axis of the piston channel; and supporting the piston in the piston channel for movement in the piston channel along the longitudinal axis of the piston channel between fill and dispense positions upon receiving a force from a drive shaft, such that:

in the fill position, the piston is moved to a position at which the second surface is laterally offset from the inlet port to allow fluid flow communication through the inlet port and into the piston channel; and in the dispense position, the piston is moved to a position at which the second surface covers the inlet port to obstruct fluid flow communication through the inlet port and to force fluid in the piston channel out of the outlet port; and fluid that is allowed to flow through the inlet port into the piston channel is conveyed through the piston channel, in a direction of the longitudinal axis of the piston channel, to the outlet port by movement of the piston in the piston channel from the fill position to the dispense position.

32. A method according to claim 31, further comprising:
arranging a one-way valve in fluid flow communication with the outlet port to allow fluid flow out from the piston channel through the outlet-port and inhibit fluid flow into the piston channel from the outlet port.

33. A method according to claim 31, further comprising connecting a reservoir having an interior volume for containing an infusion medium in fluid flow communication with inlet port of the housing of the pump device through a fluid conduit.

34. A method according to claim 33, further comprising supporting the reservoir with the first housing portion.

35. A method according to claim 31, further comprising:
providing the second housing portion with an interior volume and a wall having an opening;
supporting the drive device in the interior volume of the second housing portion, and
extending the drive shaft through the opening in the wall of the second housing portion.

36. A method according to claim 35, further comprising positioning an end of the drive shaft external to the second housing portion for operable connection with the surface of the piston, when the first housing portion and the second housing portion are engaged with each other.

* * * * *